US012799050B2

(12) United States Patent
Tinger et al.

(10) Patent No.: US 12,799,050 B2
(45) Date of Patent: Nov. 17, 2026

(54) XYLENE ISOMER SEPARATION PROCESSES

(71) Applicant: ExxonMobil Chemical Patents Inc., Spring, TX (US)

(72) Inventors: Robert G. Tinger, Friendswood, TX (US); Jonathan F. Carpency, Houston, TX (US); John S. Kennedy, Houston, TX (US); Xiaobo Zheng, Houston, TX (US)

(73) Assignee: ExxonMobil Technology and Engineering Company, Baytown, TX (US)

( * ) Notice: Subject to any disclaimer, the term of this patent is extended or adjusted under 35 U.S.C. 154(b) by 160 days.

(21) Appl. No.: 18/690,348

(22) PCT Filed: Sep. 12, 2022

(86) PCT No.: PCT/US2022/076261
§ 371 (c)(1),
(2) Date: Mar. 8, 2024

(87) PCT Pub. No.: WO2023/044278
PCT Pub. Date: Mar. 23, 2023

(65) Prior Publication Data
US 2025/0128999 A1 Apr. 24, 2025

Related U.S. Application Data

(60) Provisional application No. 63/245,044, filed on Sep. 16, 2021.

(51) Int. Cl.
*C07C 7/04* (2006.01)
*C07C 2/66* (2006.01)
*C07C 7/12* (2006.01)

(52) U.S. Cl.
CPC .................. *C07C 7/04* (2013.01); *C07C 2/66* (2013.01); *C07C 7/12* (2013.01)

(58) Field of Classification Search
None
See application file for complete search history.

(56) References Cited

U.S. PATENT DOCUMENTS 3,293,192 A 12/1966 Maher
3,308,069 A 3/1967 Wadlinger
(Continued)

FOREIGN PATENT DOCUMENTS

EP 0293032 11/1988
WO WO97/17290 5/1997
(Continued)

OTHER PUBLICATIONS

Van Bekkum, et al, Introduction to Zeolite Science and Practice, Second Completely Revised and Expanded Edition, vol. 137, pp. 1-67, Elsevier Science, B.V., Amsterdam, Netherlands (2001).

*Primary Examiner* — Vishal V Vasisth
(74) *Attorney, Agent, or Firm* — Fletcher Yoder P.C.

(57) ABSTRACT

Advantaged separation of xylene isomers may be realized by separating o-xylene and other components, such as styrene, from an aromatic hydrocarbon mixture comprising m-xylene and p-xylene. Separation of xylene isomers may comprise: providing an aromatic hydrocarbon mixture comprising at least o-xylene, m-xylene, and p-xylene; separating the aromatic hydrocarbon mixture into a first stream enriched in o-xylene and lean in m-xylene and p-xylene relative to the aromatic hydrocarbon mixture, and a second stream enriched in m-xylene and p-xylene and lean in o-xylene relative to the aromatic hydrocarbon mixture; and separating the second stream into a third stream enriched in p-xylene
(Continued)

and lean in m-xylene relative to the second stream and a fourth stream comprising m-xylene.

24 Claims, 2 Drawing Sheets

(56) References Cited

U.S. PATENT DOCUMENTS

| | | | |
|---|---|---|---|
| 3,415,736 | A | 12/1968 | Ciric |
| 3,442,795 | A | 5/1969 | Kerr |
| 3,449,070 | A | 6/1969 | McDaniel |
| 3,702,886 | A | 11/1972 | Argauer |
| 3,709,979 | A | 1/1973 | Chu |
| 3,766,093 | A | 10/1973 | Chu |
| 3,832,449 | A | 8/1974 | Rosinski |
| 3,894,104 | A | 7/1975 | Chang |
| 3,923,636 | A | 12/1975 | Mead |
| 3,948,758 | A | 4/1976 | Bonacci |
| 3,950,496 | A | 4/1976 | Ciric |
| 3,972,983 | A | 8/1976 | Ciric |
| 4,016,245 | A | 4/1977 | Plank |
| 4,021,947 | A | 5/1977 | Shneider |
| 4,076,842 | A | 2/1978 | Plank |
| 4,086,186 | A | 4/1978 | Rubin |
| 4,117,026 | A | 9/1978 | Haag |
| 4,229,424 | A | 10/1980 | Kokotailo |
| 4,254,297 | A | 3/1981 | Frenken |
| 4,310,440 | A | 1/1982 | Wilson |
| 4,356,338 | A | 10/1982 | Young |
| 4,397,827 | A | 8/1983 | Chu |
| 4,439,409 | A | 3/1984 | Puppe |
| 4,500,651 | A | 2/1985 | Lok |
| 4,619,818 | A | 10/1986 | Derouane |
| 4,623,527 | A | 11/1986 | Derouane |
| 4,632,811 | A | 12/1986 | Derouane |
| 4,639,357 | A | 1/1987 | Derouane |
| 4,639,358 | A | 1/1987 | Derouane |
| 4,664,897 | A | 5/1987 | Derouane |
| 4,673,559 | A | 6/1987 | Derouane |
| 4,698,217 | A | 10/1987 | Valyocsik |
| 4,797,267 | A | 1/1989 | Kuehl |
| 4,880,611 | A | 11/1989 | von Ballmoos |
| 4,954,325 | A | 9/1990 | Rubin |
| 5,098,684 | A | 3/1992 | Kresge |
| 5,102,643 | A | 4/1992 | Kresge |
| 5,108,725 | A | 4/1992 | Beck |
| 5,110,776 | A | 5/1992 | Chitnis |
| 5,198,203 | A | 3/1993 | Kresge |
| 5,231,064 | A | 7/1993 | Absil |
| 5,236,575 | A | 8/1993 | Bennett |
| 5,250,277 | A | 10/1993 | Kresge |
| 5,278,345 | A | 1/1994 | Janssen |
| 5,336,478 | A | 8/1994 | Dwyer |
| 5,348,643 | A | 9/1994 | Absil |
| 5,362,697 | A | 11/1994 | Fung |
| 5,476,823 | A | 12/1995 | Beck |
| 5,783,321 | A | 7/1998 | Verduijn |
| 5,972,203 | A | 10/1999 | Smith |
| 5,977,420 | A | 11/1999 | Abichandani |
| 6,077,498 | A | 6/2000 | Diaz Cabanas |
| 6,284,696 | B1 | 9/2001 | Koya |
| 6,300,535 | B1 | 10/2001 | van de Berge |
| 6,423,879 | B1 | 7/2002 | Brown |
| 6,504,072 | B1 | 1/2003 | Brown |
| 6,642,426 | B1 | 11/2003 | Johnson |
| 6,756,030 | B1 | 6/2004 | Rohde |
| 7,713,513 | B2 | 5/2010 | Jan |
| 7,842,277 | B2 | 11/2010 | Roth |
| 7,982,084 | B1 | 7/2011 | Moscoso |
| 8,704,023 | B2 | 4/2014 | Roth |
| 8,704,025 | B2 | 4/2014 | Roth |
| 9,440,893 | B2 | 9/2016 | Helton |
| 9,790,143 | B2 | 10/2017 | Runnebaum |
| 2003/0176751 | A1 | 9/2003 | Strohmaier |
| 2011/0319688 | A1 | 12/2011 | Ou |
| 2012/0108867 | A1 | 5/2012 | Pilliod |
| 2012/0108868 | A1 | 5/2012 | Pilliod |
| 2013/0158330 | A1* | 6/2013 | Corradi ..................... C07C 7/04 210/252 |
| 2013/0274532 | A1 | 10/2013 | Porter |
| 2014/0023563 | A1 | 1/2014 | Ou |
| 2015/0051430 | A1 | 2/2015 | Ou |
| 2017/0081259 | A1 | 3/2017 | Molinier |
| 2020/0308085 | A1 | 10/2020 | Washburn |

FOREIGN PATENT DOCUMENTS

| | | |
|---|---|---|
| WO | WO98/57743 | 12/1998 |
| WO | WO20/197888 | 10/2020 |

* cited by examiner

XYLENE ISOMER SEPARATION PROCESSES

CROSS-REFERENCE TO RELATED APPLICATION

This application is a national stage application under 35 USC 371 of International Application No. PCT/US2022/076261 filed on 12 Sep. 2022, which claims the benefit of priority of U.S. Provisional Patent Application No. 63/245,044, filed 16 Sep. 2021 entitled Xylene Isomer Separation Processes, the entirety of which is incorporated by reference herein.

FIELD

The present disclosure relates to separation of $C_{8+}$ aromatic hydrocarbons and, more particularly, separation of xylene isomers produced from alkylation of lower aromatic hydrocarbons and integrated processes incorporating such separation technology.

BACKGROUND $C_{8+}$ aromatic hydrocarbons, including o-, m- and p-xylene isomers, may be produced through various processes, such as via alkylation of lower aromatic hydrocarbons (e.g., benzene and/or toluene), transalkylation, toluene disproportionation, catalytic reforming, isomerization, cracking, and the like. While various processes may be utilized for alkylating lower aromatic hydrocarbons, alkylation with methanol and/or dimethyl ether under zeolite catalyst promotion may be particularly effective. Illustrative processes for alkylating lower aromatic hydrocarbons with methanol and/or dimethyl ether are described in, for example, U.S. Patent Application Publication 20200308085 and International Patent Application Publication WO/2020/197888, each of which is incorporated herein by reference. Such alkylation processes may produce p-xylene with considerably higher selectivity compared to o-xylene and m-xylene, in combination with small amounts of $C_{9+}$ aromatic hydrocarbons and byproducts such as styrene and phenol. Isomerization and other processes for producing $C_{8+}$ aromatic hydrocarbons may form an equilibrium mixture of xylene isomers containing a much smaller proportion of p-xylene.

1,4-Dimethylbenzene (p-xylene) is a valuable chemical feedstock that may be separated from $C_{8+}$ aromatic hydrocarbons. p-Xylene is used mainly for the production of terephthalic acid and polyethylene terephthalate resins, which may be used in synthetic textiles, bottles, and plastic materials among other industrial applications. As commercial applications of p-xylene have increased, the need for more selective production processes with increased p-xylene yields have risen correspondingly. Worldwide production capacity of p-xylene is about 40 million tons per year. Alkylation of lower aromatic hydrocarbons with methanol and/or dimethyl ether is one process that is supporting increased global p-xylene production.

Although styrene and phenol are usually produced in small quantities when alkylating lower aromatic hydrocarbons with methanol and/or dimethyl ether, these byproducts can be problematic to address when separating xylene isomers from one another. In conventional separation of xylene isomers produced through alkylation of lower aromatic hydrocarbons with methanol and/or dimethyl ether, a mixture of o-, m- and p-xylene isomers may be separated from $C_{9+}$ aromatic hydrocarbons, and p-xylene may then be separated from this mixture. The remaining o- and m-xylene isomers may then be catalytically isomerized to an equilibrium mixture of xylenes (a mixture of o-, m- and p-xylene isomers in about a 1:2:1 ratio) to achieve more complete conversion of feedstock into p-xylene. If not removed (e.g., with caustic or adsorption chromatography), excessive phenol may poison the isomerization catalyst. Styrene, if not removed (e.g., by clay treatment, acid catalysis, or hydrogenation), may gradually build in concentration as xylene isomers are recycled and a recycle stream is combined with freshly synthesized xylene isomers. The increasing styrene concentration may significantly raise the product volume in need of separation and necessitate the use of equipment capable of processing larger volumes than would otherwise be necessary, thereby increasing capital equipment costs. As such, conventional separation processes may employ capital equipment and/or additional processing steps, some of which may be relatively energy intensive, for promoting phenol and styrene separation, thereby increasing processing costs. Hence, alternative techniques for separating xylene isomers from one another would be desirable.

SUMMARY

In some aspects, the present disclosure provides xylene separation processes comprising: providing an aromatic hydrocarbon mixture comprising at least o-xylene, m-xylene, and p-xylene; separating the aromatic hydrocarbon mixture into a first stream enriched in o-xylene and lean in m-xylene and p-xylene relative to the aromatic hydrocarbon mixture, and a second stream enriched in m-xylene and p-xylene and lean in o-xylene relative to the aromatic hydrocarbon mixture; and separating the second stream into a third stream enriched in p-xylene and lean in m-xylene relative to the second stream and a fourth stream comprising m-xylene.

In some aspects, the present disclosure provides $C_{8+}$ aromatic hydrocarbon separation processes comprising: providing a $C_{8+}$ aromatic hydrocarbon mixture comprising at least o-xylene, m-xylene, p-xylene, styrene, optionally phenol, and $C_{9+}$ aromatic hydrocarbons; wherein the $C_{8+}$ aromatic hydrocarbon mixture comprises at least about 50 wt % p-xylene, based on total mass of the $C_{8+}$ aromatic hydrocarbon mixture; distilling the $C_{8+}$ aromatic hydrocarbon mixture to form a first stream enriched in o-xylene, styrene and $C_{9+}$ aromatic hydrocarbons and lean in m-xylene and p-xylene relative to the $C_{8+}$ aromatic hydrocarbon mixture, and a second stream enriched in m-xylene and p-xylene and lean in o-xylene relative to the $C_{8+}$ aromatic hydrocarbon mixture; and separating the second stream into a third stream enriched in p-xylene and lean in m-xylene relative to the second stream and a fourth stream comprising m-xylene.

These and other features and attributes of the disclosed methods and compositions of the present disclosure and their advantageous applications and/or uses will be apparent from the detailed description which follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

To assist one of ordinary skill in the relevant art in making and using the subject matter hereof, reference is made to the appended drawings, wherein.

DETAILED DESCRIPTION

Figure 1:
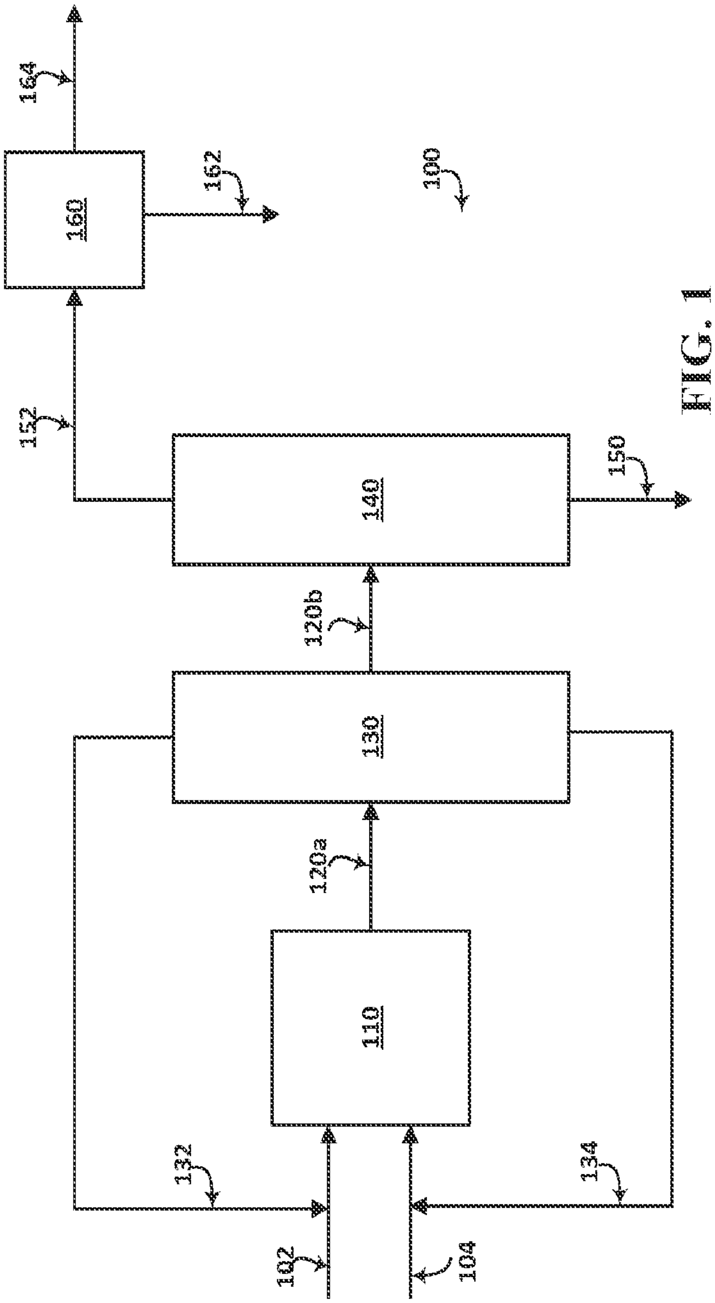
FIG. 1 is a block diagram schematically illustrating certain systems and processes of this disclosure for separating xylene isomers from an aromatic hydrocarbon mixture.

The present disclosure relates to separation of $C_{8+}$ aromatic hydrocarbons and, more particularly, separation of xylene isomers produced from alkylation of lower aromatic hydrocarbons and integrated processes incorporating such separation technology.

Definitions

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process may be described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite articles "a" or "an" shall mean "at least one" unless specified to the contrary or the context clearly indicates otherwise. Thus, for example, embodiments using "a fractionation column" include embodiments where one, two or more fractionation columns are used, unless specified to the contrary or the context clearly indicates that only one fractionation column is used.

As used herein, the term "consisting essentially of" means a composition, feed, stream or effluent that includes a given component or group of components at a concentration of at least about 60 wt %, preferably at least about 70 wt %, more preferably at least about 80 wt %, more preferably at least about 90 wt %, or still more preferably at least about 95 wt %, based on the total weight of the composition, feed, stream or effluent.

The following abbreviations may be used herein for the sake of brevity: RT is room temperature (and is 23° C. unless otherwise indicated), kPag is kilopascal gauge, psig is pound-force per square inch gauge, psia is pounds-force per square inch absolute, and WHSV is weight hourly space velocity.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, the term "hydrocarbon" means (i) any compound consisting of hydrogen and carbon atoms or (ii) any mixture of two or more such compounds in (i). The term "$C_n$ hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of such at any proportion. A "$C_m$ to $C_n$ hydrocarbon" or "$C_m$-$C_n$ hydrocarbon," where m and n are positive integers and $m<n$, means any of $C_m$, $C_{m+1}$, $C_{m+2}$, . . . , $C_{n-1}$, $C_n$ hydrocarbons, or any mixtures of two or more thereof. Thus, a "$C_2$ to $C_3$ hydrocarbon" or "$C_2$-$C_3$ hydrocarbon" can be any of ethane, ethylene, acetylene, propane, propene, propyne, propadiene, cyclopropane, and any mixtures of two or more thereof at any proportion between and among the components. A "saturated $C_2$-$C_3$ hydrocarbon" can be ethane, propane, cyclopropane, or any mixture thereof of two or more thereof at any proportion. A "$C_{n+}$ hydrocarbon" means (i) any hydrocarbon compound comprising carbon atom(s) in its molecule at the total number of at least n, or (ii) any mixture of two or more such hydrocarbon compounds in (i). A "$C_{n-}$ hydrocarbon" means (i) any hydrocarbon compound comprising carbon atoms in its molecule at the total number of at most n, or (ii) any mixture of two or more such hydrocarbon compounds in (i). A "$C_m$ hydrocarbon stream" means a hydrocarbon stream consisting essentially of $C_m$ hydrocarbon(s). A "$C_m$-$C_n$ hydrocarbon stream" means a hydrocarbon stream consisting essentially of $C_m$-$C_n$ hydrocarbon(s).

As used herein, an "aromatic hydrocarbon" is a hydrocarbon comprising an aromatic ring in the molecule structure thereof. An aromatic compound may have a cyclic cloud of pi electrons meeting the Hückel rule. A "non-aromatic hydrocarbon" means a hydrocarbon other than an aromatic hydrocarbon.

As used herein, the term "lower aromatic hydrocarbons" refers to benzene, toluene, or a mixture of benzene and toluene.

An "effluent" or a "feed" is sometimes also called a "stream" in this disclosure. Where two or more streams are shown to form a joint stream and then supplied into a vessel, it should be interpreted to include alternatives where the streams are supplied separately to the vessel where appropriate. Likewise, where two or more streams are supplied separately to a vessel, it should be interpreted to include alternatives where the streams are combined before entering into the vessel as joint stream(s) where appropriate.

The term "selectivity" refers to the degree to which a particular reaction forms a specific product, rather than another product. For example, for the methylation of toluene, 50% selectivity for p-xylene means that 50% of the products formed are p-xylene, and 100% selectivity for p-xylene means that 100% of the product formed is p-xylene. The selectivity is based on the product formed, regardless of the conversion of the particular reaction. The selectivity for a given product produced from a given reactant can be defined as weight percent (wt %) of that product relative to the total weight of the products formed from the given reactant in the reaction.

As used herein, the term "liquid-phase" means reaction conditions in which aromatic hydrocarbons present in a reactor are substantially in a liquid state. "Substantially in liquid phase" means ≥about 90 wt %, preferably ≥about 95 wt %, preferably ≥about 99 wt %, and preferably the entirety of the aromatic hydrocarbons, is in liquid phase.

As used herein, the term "vapor-phase" means reaction conditions in which aromatic hydrocarbons present in a reactor are substantially in a vapor state. "Substantially in vapor phase" means ≥about 90 wt %, preferably ≥about 95 wt %, preferably ≥about 99 wt %, and preferably the entirety of the aromatic hydrocarbons, is in vapor phase.

As used herein, the term "alkylation" means a chemical reaction in which an alkyl group is transferred to an aromatic ring as a substitute group thereon from an alkyl group source compound. "Methylation" means alkylation in which the transferred alkyl group is a methyl. Thus, methylation of benzene can produce toluene, xylenes, trimethylbenzenes, and the like; and methylation of toluene can produce xylenes, trimethylbenzenes, and the like.

"Methylated aromatic hydrocarbon" means an aromatic hydrocarbon comprising at least one methyl group and only methyl group(s) attached to the aromatic ring(s) therein. Examples of methylated aromatic hydrocarbons include toluene, xylenes, trimethylbenzenes, tetramethylbenzenes, pentamethylbenzene, hexamethylbenzene, methylnaphthalenes, dimethylnaphthalenes, trimethylnaphthalenes, tetramethylnaphthalenes, and the like.

In this disclosure, o-xylene means 1,2-dimethylbenzene, m-xylene means 1,3-dimethylbenzene, and p-xylene means 1,4-dimethylbenzene. Herein, the generic term "xylene(s)," either in singular or plural form, collectively means one of or any mixture of two or three of p-xylene, m-xylene, and o-xylene at any proportion thereof.

As used herein, the term "rich" or "enriched," when describing a component in a stream, means that the stream comprises the component at a concentration higher than a source material from which the stream is derived. As used herein, the term "depleted" or "lean," when describing a component in a stream, means that the stream comprises the component at a concentration lower than a source material from which the stream is derived.

Unless otherwise specified herein, any stream herein that is "rich" in a particular component may "consist of" or "consist essentially of" that component. "Consisting essentially of," as used herein, means that a composition, feed, stream or effluent comprises a given component at a concentration of at least about 60 wt %, preferably at least about 70 wt %, more preferably at least about 80 wt %, more preferably at least about 90 wt %, still more preferably at least about 95 wt %, based on the total mass of the composition, feed, stream or effluent in question.

Unless otherwise specified herein, any stream that is "lean" in a particular component may be "free of" or "substantially free of" that component. "Essentially free of" and "substantially free of," as interchangeably used herein, mean that a composition, feed, stream or effluent comprises a given component at a concentration of at most about 10 wt %, preferably at most about 8 wt %, more preferably at most about 5 wt %, more preferably at most about 3 wt %, still more preferably at most about 1 wt %, based on the total mass of the composition, feed, stream or effluent in question.

As used herein, the term "molecular sieve" means a crystalline or semi-crystalline substance, such as a zeolite, with pores of molecular dimensions that permit the passage of molecules below a certain size.

As used herein, the term "aviation gasoline" or "AvGas" interchangeably means a fuel composition suitable for internal combustion engines of airborne vehicles. Specifications for AvGas are provided in, for example, ASTM D910 and various government regulations such as those from the Federal Aviation Administration of the United States.

In this disclosure, "motor octane number" is determined by ASTM D2700. When used alone herein, "octane" and "octane number" mean motor octane number. Motor octane number is sometimes abbreviated as "MON" herein. A "high octane number" means a MON≥about 95, preferably ≥about 96, more preferably ≥about 97, more preferably ≥about 98, more preferably ≥about 99, and still more preferably ≥about 100. Pure p-xylene, o-xylene, m-xylene, ethylbenzene, and 1,3,5-trimethylbenzene have MONs of about 105, 85-94, 105, 90-102, and 120, respectively. As such, p-xylene, m-xylene, and trimethylbenzenes are more preferable than o-xylene and ethylbenzene as ingredients of a high-octane-number fuel component from the perspective of octane number of the fuel composition formulated from the fuel component, especially if a high octane number of ≥about 98 is desired for the fuel composition.

Xylene Separation Processes

As discussed above, conventional separation processes for xylene mixtures produced from alkylation of lower aromatic hydrocarbons with methanol and/or dimethyl ether may be complicated by co-production of phenol and styrene. The former may poison an isomerization catalyst used for improving overall yield of a particular xylene isomer (e.g., p-xylene), and the latter (or a reacted form thereof) may accumulate during processing of various recycle streams and poison zeolites used in the xylene production process steps. Removal of phenol and styrene may be conducted to address these concerns, but doing so may make the separation process more complicated and expensive.

The present disclosure provides advantaged processes for separating xylene isomers from one another. In the present disclosure, xylene isomer separation processes are described in which o-xylene is initially separated from m-xylene and p-xylene, after which point the remaining m-xylene and p-xylene become more readily separable from each other, as described in further detail hereinafter. Since the m-xylene and p-xylene may be readily separated from each other and processed into value products, recycling and isomerization of mixed xylenes is no longer needed to achieve more complete conversion to p-xylene, particularly since p-xylene may be produced with high selectivity when alkylating toluene with methanol and/or dimethyl ether under conditions described further herein. As non-limiting examples, separation of m-xylene and p-xylene from one another may take place by simulated moving bed chromatography or crystallization, as described in greater detail hereinbelow. Initial separation of o-xylene from m-xylene and p-xylene may be accomplished with an efficient distillation column and process, as described in detail hereinbelow. The distillation process may provide o-xylene as a bottoms fraction in combination with $C_{9+}$ aromatic hydrocarbons, and a mixture of m-xylene and p-xylene may be obtained as an overhead fraction. Other suitable techniques for separating o-xylene from a mixture of m-xylene and p-xylene may include adsorption chromatography or membrane separation, for example.

By separating o-xylene initially, a number of advantages may be realized in the overall separation of xylene isomers from an aromatic hydrocarbon mixture. Since a downstream isomerization reaction is no longer needed after separating o-xylene initially, particularly when starting from an aromatic hydrocarbon mixture already having a high fraction of p-xylene, the presence of a phenolic byproduct is no longer an issue because there is no need to protect a downstream isomerization catalyst in most process configurations. In addition, the styrene byproduct tends to co-distill predominantly with o-xylene in the bottoms fraction, such that the amount of styrene obtained in the overhead fraction in combination with m-xylene and p-xylene is not problematic for further separation of these materials. Moreover, by avoiding a recycle stream to increase p-xylene production, accumulation of styrene or reduced products thereof is no longer an issue. As such, there is no critical need to remove phenol or styrene byproducts in the processes disclosed herein. Thus, smaller equipment and lower capital expenditure may be realized with the processes disclosed herein.

As indicated above, o-xylene and m-xylene may be formed in much lower amounts than is p-xylene when alkylating lower aromatic hydrocarbons with methanol and/or dimethyl ether. Although o-xylene and m-xylene may be formed in lower amounts when alkylating lower aromatic hydrocarbons, value products may still be obtained from the streams containing these separated xylene isomers, as produced in the disclosure herein. For example, the bottoms fraction may be optionally fractionated to separate o-xylene from $C_{9+}$ aromatic hydrocarbons and styrene (optionally after conversion of styrene into heavy aromatic byproducts, such as through clay treatment or acid treatment, or hydrogenation to form ethylbenzene). o-Xylene may be subsequently converted to phthalic acid, for example. m-Xylene recovered from simulated moving bed chromatography or another suitable separation technique may be of sufficient purity to serve as a precursor to isophthalic acid, or be utilized directly as a fuel component (e.g., within a high-octane motor gasoline blend or as an AvGas co-blend). A portion of the o-xylene may be optionally blended with a portion of the m-xylene to form a mixture suitable for a high-octane motor gasoline blend or an AvGas co-blend. Optionally, either o-xylene or m-xylene obtained by the processes disclosed herein may be further isomerized if a higher p-xylene output is desired, provided that phenol and/or styrene therein are adequately addressed before performing the isomerization. In a preferred embodiment, o-xylene may be isomerized by using LPI, in which unwanted side reactions are low. LPI effluent can be directly processed to p-xylene recovery without the need to fraction out the heavy components in the isomerate. Further isomerization of the o-xylene and/or m-xylene may take place during parallel processing of an aromatic hydrocarbon stream through isomerization, wherein the parallel-processed aromatic hydrocarbon stream is related or unrelated to the aromatic hydrocarbon mixture providing the xylene isomers undergoing separation according to the disclosure herein. A related aromatic hydrocarbon stream may directly or indirectly provide the lower aromatic hydrocarbons being converted into the xylenes in the aromatic hydrocarbon mixture undergoing separation according to the disclosure herein, for example. Related aromatic hydrocarbon streams that may be processed in parallel are discussed further herein.

Before discussing more particular aspects of the foregoing in further detail, the processes of the present disclosure will be described in reference to the drawings.

FIG. 1 is a block diagram schematically illustrating certain systems and processes 100 for separating xylene isomers from an aromatic hydrocarbon mixture according to the present disclosure. In FIG. 1 showing process 100, lower aromatic hydrocarbon feed 102 is provided to alkylation reactor 110 containing an alkylation catalyst. Lower aromatic hydrocarbon feed 102 may comprise benzene, toluene, or a mixture of benzene and toluene. Alkylation feed 104 comprising an alkylating agent such as methanol and/or dimethyl ether is concurrently provided to alkylation reactor 110 and reacted with lower aromatic hydrocarbon feed 102 under alkylation conditions. Suitable alkylation catalysts and alkylation conditions are discussed further hereinbelow. Alkylation stream 120*a* exits alkylation reactor 110 and comprises a mixture of xylene isomers (preferably, predominantly p-xylene), water, and unreacted lower aromatic hydrocarbons or lower aromatic hydrocarbons that have not been fully converted to $C_{8+}$ aromatic hydrocarbons. Optionally, residual alkylating agent, such as methanol and/or dimethyl ether, may be present in alkylation stream 120*a*. If desired or needed, unreacted lower aromatic hydrocarbons and/or residual alkylating agent within alkylation stream 120*a* may be separated from the mixture of xylene isomers using separation sub-system 130 (which may utilize at least one column), lower aromatic hydrocarbon recycle stream 132 may be returned to alkylation reactor 110 in conjunction with lower aromatic hydrocarbon feed 102, and alkylating agent recycle stream 134 may be returned to alkylation reactor 110 together with alkylation feed 104. As such, lower aromatic hydrocarbon recycle stream 132 may be provided as at least a portion of lower aromatic hydrocarbon feed 102. Lower aromatic hydrocarbon recycle stream may comprise a toluene-rich stream in some examples.

Alkylation stream 120*b* exits separation sub-system 130 and is provided to o-xylene separator 140. As discussed above, alkylation stream 120*b* comprises at least o-xylene, m-xylene, and p-xylene and may further comprise phenol and styrene. o-Xylene separator 140 may include any column that is capable of effectively separating o-xylene from a mixture of m-xylene and p-xylene under suitable process conditions. o-Xylene separator 140 may be a column containing a plurality of trays, or the column may be a packed column. In addition, o-xylene separator 140 may be multiple columns, which may individually contain a plurality of trays, appropriate packing, or any combination thereof. When o-xylene separator 140 is a tray-based column containing a plurality of trays, a sufficient number of trays may be present to afford a sufficient degree of o-xylene separation based upon an amount of energy input thereto. In non-limiting examples, suitable tray-based columns may contain at least about 100 separation trays, or at least about 120 separation trays, or at least about 140 separation trays, or at least about 160 separation trays, or at least about 180 separation trays, or at least about 200 separation trays, up to a maximum number of trays that can physically be incorporated in the column.

Alternately or additionally, o-xylene separator 140 may perform separation of alkylation stream 120*b* (or alkylation stream 120*a*) through membrane separation, adsorption chromatography, or any combination thereof.

Upon separating alkylation stream 120*b* (or alkylation stream 120*a*) in a column of o-xylene separator 140, a mixture predominantly comprising o-xylene and $C_{9+}$ aromatic hydrocarbons may be obtained as bottoms fraction 150, and a mixture comprising predominantly m-xylene and p-xylene may be obtained as overhead fraction 152. As such, bottoms fraction 150 may be enriched in o-xylene and lean in m-xylene and p-xylene relative to an aromatic hydrocarbon mixture within lower aromatic hydrocarbon feed 102. Bottoms fraction 150 may further comprise styrene or a reacted form thereof (e.g., heavy aromatic hydrocarbons) and may be carried along as bottoms fraction 150 is further processed. At least a majority of the styrene in the aromatic hydrocarbon mixture may enter bottoms fraction 150, and preferably at least about 90% of the styrene present in the aromatic hydrocarbon mixture enters bottoms fraction 150. o-Xylene may be further separated from bottoms fraction 150 to provide an o-xylene stream, if desired, or bottoms fraction 150 may be further processed in an alternative manner.

In process 100 of FIG. 1, overhead fraction 152 is provided to p-xylene separation unit 160, which may employ a simulated moving bed chromatography separation unit or a crystallization separation unit, in which m-xylene stream 162 and p-xylene stream 164 may be at least partially separated from one another. Given the high percentage of p-xylene produced in alkylation reactor 110 when alkylating lower aromatic hydrocarbon feed 102 with methanol and/or dimethyl ether as alkylation feed 104, p-xylene stream 164 may represent a majority stream and m-xylene stream 162 may be a minority stream obtained from p-xylene separation unit 160. In addition, the separation performed in p-xylene separation unit 160 may localize minor impurities (e.g., phenol or ethylbenzene) from overhead fraction 152 in one of p-xylene stream 164 or m-xylene stream 162 but substantially not in the other. When p-xylene separation unit 160 comprises a simulated moving bed chromatography separation unit, m-xylene stream 162, which may be referred to as a raffinate stream, may comprise m-xylene at a high concentration such as, for example, ≥about 90%, ≥about 95%, or ≥about 98%, based on the total mass of m-xylene stream 162. Such a high-concentration m-xylene stream 162 can be advantageously sold as is for use as an aviation gasoline blending component, for conversion into isophthalic acid, and the like. When p-xylene separation unit 160 comprises a crystallization separation unit, m-xylene stream 162, which may be referred to as a filtrate stream, may comprise m-xylene at various concentrations such as, for example, ≥about 60%, ≥about 70%, or ≥about 80%, based on total mass of m-xylene stream 162, in combination with some residual p-xylene. In the case of m-xylene stream 162 comprising high concentrations of both p-xylene and m-xylene and a low concentration of o-xylene (preferably substantially free of o-xylene), m-xylene stream 162 can be advantageously used as an aviation gasoline blending stock, or recycled to a crystallization separation unit or a simulated moving bed chromatography separation unit to recover an additional quantity of p-xylene therefrom.

Figure 2:
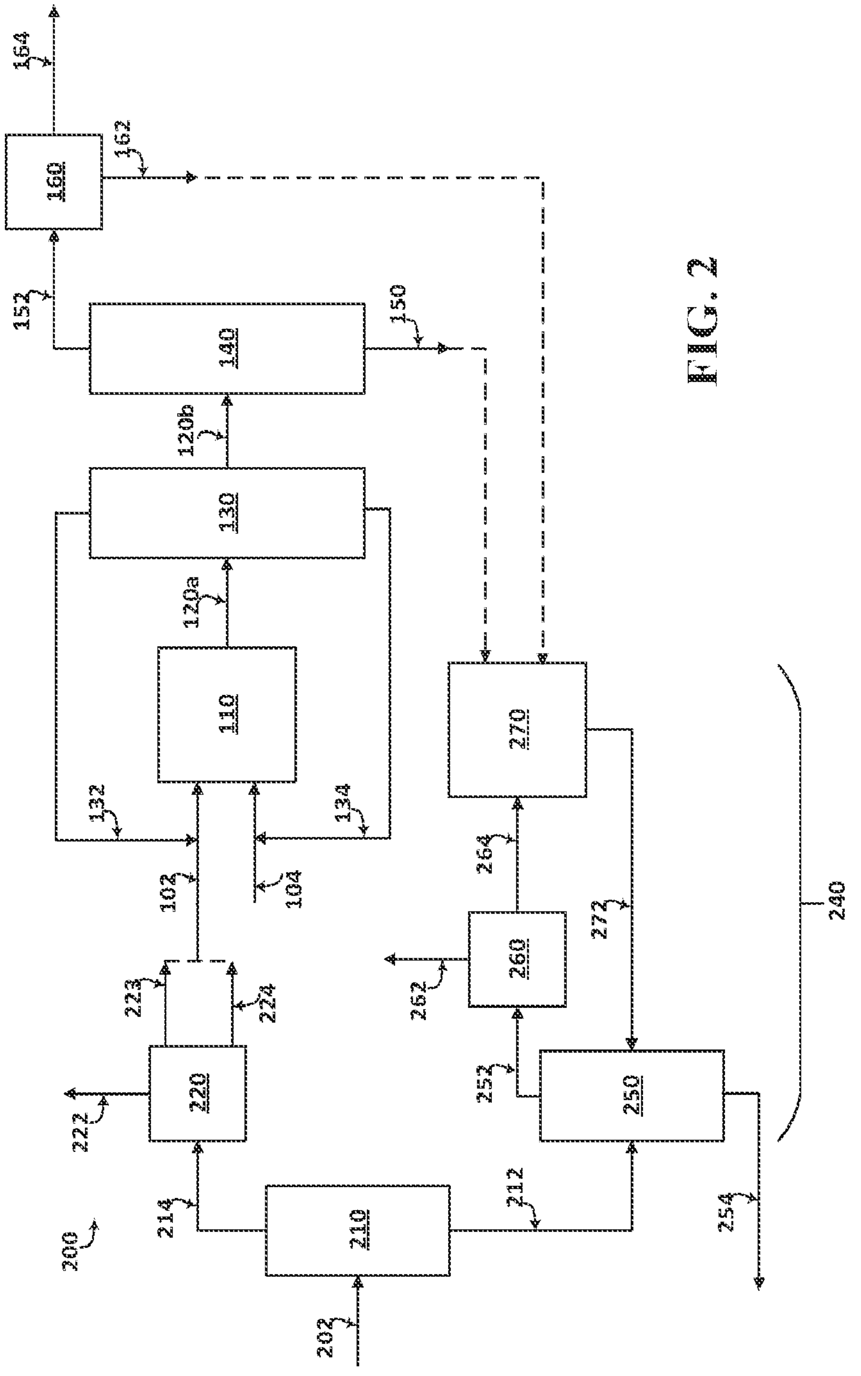
FIG. 2 is a block diagram schematically illustrating certain systems and processes of this disclosure for producing and separating xylene isomers formed from lower aromatic hydrocarbons obtained from a reformate stream.

Lower aromatic hydrocarbon feed 102 may be produced in conjunction with a reforming process, and process 100 may be coupled to a reforming process, as discussed below in reference to FIG. 2. As shown in FIG. 2 for process 200, reformate feed stream 202 comprising $C_{6+}$ hydrocarbons is first separated at reformate splitter 210, which may employ one or more columns, to provide $C_{8+}$ aromatics stream 212 and lower aromatic hydrocarbon stream 214 as at least one of a benzene stream, a toluene stream, or a mixed benzene/toluene stream, in combination with non-aromatic byproducts. Lower aromatic hydrocarbon stream 214 may be referred to as a $C_{7-}$ hydrocarbon stream. Lower aromatic hydrocarbon stream 214 is then separated via extraction in unit 220 to produce stream 222 rich in non-aromatic byproducts and purified lower aromatic hydrocarbons, which may include stream 223 rich in benzene and stream 224 rich in toluene, or streams 223 or 224 may be combined and comprise a mixture rich in both toluene and benzene. Streams 223 and 224, or a combined stream rich in benzene and toluene, may then be provided as at least a portion of lower aromatic hydrocarbon feed 102 to alkylation reactor 110. Xylene isomers produced in alkylation reactor 110 may then be separated from one another in a manner identical to that described above for process 100 in FIG. 1.

$C_{8+}$ aromatics stream 212 is introduced to xylenes loop 240 and separated via xylenes splitter 250, which may comprise at least one column, to produce overhead fraction 252 rich in $C_8$ aromatic hydrocarbons (e.g., a mixture of o-, m- and p-xylene) and bottoms fraction 254 rich in $C_{9+}$ aromatic hydrocarbons. Overhead fraction 252 may be provided to p-xylene separation unit 260, which may employ a simulated moving bed chromatography separation unit or a crystallization separation unit similar to those described above in connection with FIG. 1, to separate p-xylene stream 262 and mixed o-xylene/m-xylene stream 264 from one another. Mixed o-xylene/m-xylene stream 264 is then provided to isomerization unit 270, which produces an equilibrium xylene mixture under isomerization reaction conditions in the presence of a suitable isomerization catalyst. The equilibrium xylenes mixture may be provided as recycle stream 272 and returned to xylenes splitter 250 for further processing with $C_{8+}$ aromatics stream 212. Small amounts of $C_{9+}$ aromatic hydrocarbons produced in isomerization unit 270 are also returned to xylenes splitter 250 with recycle stream 272 and undergo separation therein into bottoms fraction 254. Xylenes splitter 250, p-xylene separation unit 260, and isomerization unit 270 together define a main portion of xylenes loop 240. Since the $C_{8+}$ aromatic hydrocarbons within $C_{8+}$ aromatics stream 212 are obtained via reforming, rather than via alkylation with methanol and/or dimethyl ether, substantial quantities of phenol and/or styrene are not typically introduced into xylenes loop 240, and there is no risk associated with protecting the isomerization catalyst in isomerization unit 270.

Optionally, at least a portion of o-xylene and/or m-xylene obtained from alkylation reactor 110 and separated as above (i.e., within bottoms fraction 150 or m-xylene stream 162, either as a raffinate stream or a crystallization stream) may be transferred to xylenes loop 240 and further processed therein, provided that phenol and/or styrene is/are removed therefrom prior to being introduced to xylenes loop 240. For example, styrene in bottoms fraction 150 may be treated with clay or an acidic catalyst to convert the styrene into heavy aromatic compounds or hydrogenated to produce ethylbenzene, and phenol in m-xylene stream 162 may be removed by passage through a fixed bed of sorbent, such as alumina, and/or treatment with caustic. Styrene or heavy aromatic compounds formed from styrene may be removed using an additional column prior to being introduced to xylenes loop 240 (additional column not shown). Bottoms fraction 150 and/or m-xylene stream 162 may be introduced to xylenes loop 240 together or separately (separate introduction shown in FIG. 2). Moreover, although bottoms fraction 150 and/or m-xylene stream 162 are shown in FIG. 2 as being introduced to isomerization unit 270, it is to be appreciated that other points of introduction into xylenes loop 240 are possible and the depicted location should not be considered limiting. For instance, bottoms fraction 150 and/or m-xylene stream 162 may be introduced to xylenes splitter 250, by way of non-limiting example.

Accordingly, separation processes of the present disclosure may comprise providing an aromatic hydrocarbon mixture comprising at least o-xylene, m-xylene, and p-xylene; separating the aromatic hydrocarbon mixture into a first stream enriched in o-xylene and lean in m-xylene and p-xylene relative to the aromatic hydrocarbon mixture, and a second stream enriched in m-xylene and p-xylene and lean in o-xylene relative to the aromatic hydrocarbon mixture; and separating the second stream into a third stream enriched in p-xylene and lean in m-xylene relative to the second stream and a fourth stream comprising m-xylene.

Separation of the aromatic hydrocarbon mixture into the first stream and the second stream may take place via any suitable technique sufficient to separate o-xylene from a mixture of m-xylene and p-xylene. In illustrative embodiments, separating the aromatic hydrocarbon mixture into the first stream and the second stream may take place in a distillation column, such that the first stream comprising o-xylene is obtained as a bottoms fraction and the second stream comprising a mixture of m-xylene and p-xylene is obtained as an overhead fraction. In illustrative embodiments, the distillation column for separating o-xylene from the mixture of m-xylene and p-xylene may be a tray-based distillation column comprising at least about 140 separation trays. Because the xylenes mixture produced from a benzene/toluene alkylation process (e.g., alkylation with methanol and/or dimethyl ether) tends to have an m-xylene/o-xylene ratio higher than an equilibrium xylenes mixture, separation of o-xylene therefrom using a distillation column can be easier than separation of the same from an equilibrium xylenes mixture. One skilled in the art will understand there is a tradeoff between energy consumption and the number of fractionation stages.

Other suitable techniques for separating o-xylene from a mixture of m-xylene and p-xylene may include, for example, absorption chromatography, membrane separation, or the like.

Depending on the source from which it is obtained or produced, the aromatic hydrocarbon mixture may further comprise $C_{9+}$ aromatic hydrocarbons, styrene, and/or phenol. Exemplary aromatic hydrocarbon mixtures suitable for separation according to the disclosure herein may be obtained through alkylation of toluene with methanol and/or dimethyl ether under alkylation conditions, as discussed further hereinbelow. The aromatic hydrocarbon mixture includes all feed streams fed into the separation conducted to produce the first stream and the second stream. A single stream comprising o-xylene, m-xylene, and p-xylene and optionally $C_{9+}$ aromatic hydrocarbons may be fed into the separation. Alternately, multiple streams having differing compositions may be combined to form a single joint stream, which is then fed into the separation. Further alternately, multiple streams having differing compositions may be fed into a separation column at multiple, differing locations on the separation column. For example, a stream consisting essentially of $C_8$ aromatic hydrocarbons may be fed into the separation column at first feed inlet, and a separate stream consisting essentially of $C_{9+}$ aromatic hydrocarbons may be fed into the same separation column at a second feed inlet lower than the first feed inlet. When multiple aromatic hydrocarbon streams are separated concurrently, the "aromatic hydrocarbon mixture" should be understood as the aggregate of the multiple aromatic hydrocarbon streams fed into the same separation column.

The aromatic hydrocarbon mixture may comprise o-xylene at various concentrations ranging from c1 wt % to c2 wt %, based on the total mass of the aromatic hydrocarbon mixture, where c1 and c2 can be, independently, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 80, as long as $c1<c2$. Desirably, at least a majority, preferably ≥about 55%, preferably ≥about 60%, preferably ≥about 65%, preferably ≥about 70%, preferably ≥about 75%, preferably ≥about 80%, preferably ≥about 85%, preferably ≥about 90%, preferably ≥about 91%, preferably ≥about 92%, preferably ≥about 93%, preferably ≥about 94%, preferably ≥about 95%, preferably ≥about 96%, preferably ≥about 97%, preferably ≥about 98%, preferably ≥about 99%, of the o-xylene present in the aromatic hydrocarbon mixture (i.e., the total o-xylene fed into the separation column) may enter into the first stream (e.g., as a bottoms stream from the separation column).

When present in the aromatic hydrocarbon mixture, at least a majority of the styrene and/or $C_{9+}$ aromatic hydrocarbons may enter the first stream, such as in a bottoms fraction obtained from a distillation column. In illustrative embodiments, the aromatic hydrocarbon mixture may comprise up to about 5000 ppm styrene by weight, such as about 10 ppm to about 5000 ppm styrene by weight or about 1000 ppm to about 2000 ppm styrene by weight, based on total mass of the aromatic hydrocarbon mixture. Desirably, at least a majority, preferably ≥about 55%, preferably ≥about 60%, preferably ≥about 65%, preferably ≥about 70%, preferably ≥about 75%, preferably ≥about 80%, preferably ≥about 85%, preferably ≥about 90%, preferably ≥about 91%, preferably ≥about 92%, preferably ≥about 93%, preferably ≥about 94%, preferably ≥about 95%, preferably ≥about 96%, preferably ≥about 97%, preferably ≥about 98%, preferably ≥about 99%, of the styrene present in the aromatic hydrocarbon mixture (i.e., the total styrene fed into the separation column) enters into the first stream (e.g., a bottoms stream from the separation column). Preferably, the second stream may comprise about 50 ppm styrene by weight or less (preferably ≤about 40 ppm, preferably ≤about 30 ppm, preferably ≤about 20 ppm, preferably ≤about 10 ppm, preferably ≤about 5 ppm), based on total mass of the second stream.

In non-limiting examples, the aromatic hydrocarbon mixture comprising xylenes may be obtained as at least a portion of a cracking stream, a reformate stream, an aromatic alkylation stream (e.g., by alkylating lower aromatic hydrocarbons with methanol and/or toluene under suitable conditions), an aromatic transalkylation stream, an aromatic isomerization stream, a toluene disproportionation stream, or any combination thereof. Optionally, a stream obtained from any of the foregoing may be further processed prior to being provided as the aromatic hydrocarbon mixture or a portion thereof for separation according to the disclosure herein. Further optionally, a first stream obtained from any of the foregoing may be provided as the aromatic hydrocarbon mixture or as a lower aromatic hydrocarbon stream for conversion into the aromatic hydrocarbon mixture, and a second stream obtained from any of the foregoing may be processed in parallel to achieve higher feed conversion. More specific details are provided hereinbelow.

If desired, o-xylene may be separated from the second stream as a value material. In particular, the second stream, such as a bottoms fraction obtained from distillation, may be separated into a fifth stream enriched in o-xylene and lean in $C_{9+}$ aromatic hydrocarbons and styrene relative to the first stream and a sixth stream enriched in $C_{9+}$ aromatic hydrocarbons and optionally styrene and lean in o-xylene relative to the first stream. Separation into the fifth and sixth streams may be conducted via distillation, adsorption chromatography, or the like, in non-limiting examples. When separated into fifth and sixth streams, the fifth stream may comprise o-xylene in an amount of at least about 80 wt % based on total mass of the fifth stream, or at least about 85 wt %, or at least about 90 wt %, or at least about 95 wt %, or at least about 96 wt %, or at least about 97 wt %, or at least about 98 wt %, or at least about 99 wt %. In some embodiments, the fifth stream may consist essentially of o-xylene. As still another option, discussed further below, the second stream (or o-xylene separated therefrom in a fifth stream) may be isomerized into an equilibrium mixture of xylene isomers. The sixth stream enriched in $C_{9+}$ aromatic hydrocarbons may be supplied to a transalkylation unit together with a lower aromatic hydrocarbon stream, from which an additional quantity of xylenes may be produced. The transalkylation effluent, or a portion thereof, may be fed into a xylenes splitter, such as that present within xylenes loop 240 (see FIG. 2).

A ratio of the total amount of o-xylene in the first stream to the total amount of o-xylene in the second stream may range from r1 to r2, where r1 and r2 can be, independently, for example, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, or 50, as long as r1<r2. Preferably r1 is greater than or equal to about 1. More preferably r1 is greater than or equal to about 2. Still more preferably r1 is greater than or equal to about 5. Still more preferably r1 is greater than or equal to about 10. A low concentration of o-xylene in the second stream compared to the o-xylene concentration in the first stream may be conducive for the production of a high-octane blending component using the processes of this disclosure, such as an m-xylene stream or a p-xylene stream as an AvGas blending component.

Separation of the aromatic hydrocarbon mixture comprising $C_{8+}$ aromatic hydrocarbons may take place using any suitable technique capable of achieving sufficient resolution of m-xylene and p-xylene in a second stream from o-xylene and $C_{9+}$ aromatic hydrocarbons, and optionally styrene, in a first stream. The first stream obtained from the separation is rich in o-xylene and lean in p-xylene and m-xylene compared to the aromatic hydrocarbon mixture, and the second stream is rich in p-xylene and m-xylene and lean in o-xylene compared to the aromatic hydrocarbon mixture. In some embodiments, separation may take place using one or more distillation columns by virtue of the separation in boiling points of the xylene isomers (o-xylene, m-xylene, and p-xylene have normal boiling points of 144° C., 139° C., and 138° C., respectively). As such, the higher boiling o-xylene may be obtained within a bottoms fraction through use of a sufficiently efficient distillation column and distillation process. In addition or alternately, separation of the aromatic hydrocarbon mixture may utilize separation techniques such as membrane separation or adsorption chromatographic separation.

The second stream, which is enriched in m-xylene and p-xylene and lean in o-xylene, such as an overhead fraction obtained from distillation, may be processed to at least partially separate m-xylene and p-xylene from one another as other streams are being processed. Optionally, the o-xylene stream can blended into the second stream up to 20% of o-xylene to produce an AvGas blend stock. Depending on the intended end application for the p-xylene and m-xylene being separated within the third and fourth streams, respectively, that are obtained from the second stream, the amount of residual o-xylene in the second stream may be up to about 3.5 wt % based upon total mass of the second stream. For example, if the third stream or the fourth stream are being utilized as an AvGas blending component, up to about 20 wt % o-xylene may be tolerated in the third stream or the fourth stream, in which case the amount of o-xylene in the second stream may be up to about 3.5 wt %. In other instances, however, the amount of o-xylene in the second stream may be about 3 wt % or less, or about 2.5 wt % or less, or about 2 wt % or less, or about 1.5 wt % or less, or about 1 wt % or less, or about 0.5 wt % or less, or about 0.1 wt % or less, based on total mass of the second stream. In some examples, the second stream may comprise o-xylene in a non-zero amount up to about 1000 ppm by weight, based on total mass of the second stream.

After being separated from the aromatic hydrocarbons mixture, the second stream may be separated into the third stream and the fourth stream to at least partially separate the m-xylene and the p-xylene from each other. The second stream comprising m-xylene and p-xylene may be directly separated into the third stream comprising p-xylene, such as enriched in p-xylene and lean in m-xylene, and the fourth stream comprising m-xylene, such as enriched in m-xylene and lean in p-xylene. The third stream may comprise p-xylene as a majority component and define a p-xylene stream, optionally consisting essentially of p-xylene, and the fourth stream may comprise m-xylene as a majority component and define an m-xylene stream. In non-limiting examples, separation of the second stream into the third stream and the fourth stream may take place by simulated moving bed chromatography, crystallization, absorption chromatography, or any combination thereof. In at least the case of crystallization, the third stream may be enriched in p-xylene and lean in m-xylene, optionally consisting essentially of p-xylene, and the fourth stream may comprise a mixture of m-xylene and p-xylene, in which m-xylene is present in a greater amount than is p-xylene.

In some embodiments, separation of the second stream into the third stream and the fourth stream may take place using simulated moving bed chromatography in a simulated moving bed chromatography separation unit, details of which will be familiar to one having ordinary skill in the art. Commercially available simulated moving bed chromatography processes are available from Axens, a French corporation, as ELUXYL® technology.

When produced by a simulated moving bed chromatography separation unit, the third stream may comprise p-xylene at a concentration of ≥about 95%, ≥about 97%, ≥about 98%, ≥about 99%, ≥about 99.5%, or even ≥about 99.7%, based on the total mass of the third stream.

When produced by a simulated moving bed chromatography separation unit, the fourth stream may comprise m-xylene at a concentration of ≥about 90%, ≥about 92%, ≥about 94%, ≥about 95%, ≥about 97%, or ≥about 99%, based on the total mass of the fourth stream. A high-purity m-xylene stream, such as the fourth stream or a further purified fourth stream, may be utilized for making isophthalic acid (benzene-1,3-dicarboxylic acid), which can be used for making PET resin, polybenzimidazole, and the like, or as a blending stock for an aviation gasoline.

In other embodiments, the second stream may be separated into the third stream and the fourth stream using crystallization in a crystallization separation unit. Crystallization techniques may take advantage of the much higher melting point of p-xylene (13° C.) compared to o-xylene (−25° C.), m-xylene (−48° C.), and ethylbenzene (−95° C.). By cooling the second stream to a temperature lower than the p-xylene crystallization temperature (melting point), p-xylene may preferentially crystallize from a mixture of p-xylene and m-xylene, optionally containing other impurities. The p-xylene may then be separated from the filtrate (fourth stream comprising a mixture of m-xylene and p-xylene) by filtration, centrifugation, decantation, and like techniques. The p-xylene (third stream) may optionally be further purified by melting and recrystallization, if desired, to produce a high purity p-xylene product. Description of crystallization-based p-xylene purification processes can be found in, for example, Handbook of Petrochemicals Production Processes, Second Edition, by Robert A. Meyers, Ph.D., Chapter 1.5, the relevant contents of which are incorporated herein by reference.

When produced by a crystallization unit, the third stream may comprise p-xylene at a concentration of ≥about 95%, ≥about 97%, ≥about 98%, ≥about 99%, ≥about 99.5%, or even ≥about 99.7%, based on the total mass of the third stream.

When produced by a crystallization unit, the fourth stream may comprise p-xylene at a concentration from c(pX)5 wt % to c(pX)6 wt %, and m-xylene at a concentration from c(mX)5 wt % to c(mX)6 wt %, based on the total mass of the fourth stream, wherein c(pX)5 and c(pX)6 can be, independently, for example, 8, 9, 10, 11, 12, 13, 14, 15, 16, 18, 20, 22, 24, 25, 26, 28, 30, 32, 34, as long as c(pX)5<c(pX)6; and c(mX)5 and c(mX)6 can be, independently, for example, 60, 65, 70, 75, 80, 85, 90, 91, 92, as long as c(mX)5<c(mX)6. Due to its relatively low concentrations of p-xylene and o-xylene, such a fourth stream may be advantageous for use as a high-octane fuel component, such as an AvGas blending component. Optionally, the fourth stream may be further purified, if desired, to isolate m-xylene and/or p-xylene therefrom.

In still another example, the second stream may be separated into the third stream and the fourth stream using adsorption chromatography or membrane separation technology. In such embodiments, the fourth stream may comprise p-xylene at a concentration from c(pX)3 wt % to c(pX)4 wt %, and m-xylene at a concentration from c(mX)3 wt % to c(mX)4 wt %, based on the total mass of the fourth stream, wherein c(pX)3 and c(pX)4 can be, independently, for example, 0, 0.1, 0.2, 0.4, 0.5, 0.6, 0.8, 1, 2, 3, 4, 5, as long as c(pX)3<c(pX)4; and c(mX)3 and c(mX)4 can be, independently, for example, 60, 65, 70, 75, 80, 85, 90, 91, 92, 93, 94, 95, as long as c(mX)3<c(mX)4. Due to its relatively low concentrations of p-xylene and o-xylene, the fourth stream may be advantageous for use as a high-octane fuel component, such as an AvGas blending component. Optionally, the fourth stream may be further purified, if desired, to isolate m-xylene and/or p-xylene therefrom.

The third stream produced in any of the foregoing may comprise p-xylene in sufficient purity to support various applications, such as for conversion into other value products (e.g., terephthalic acid). Optionally, if desired, the p-xylene obtained within the third stream may be further purified by techniques known to persons having ordinary skill in the art.

The separation processes disclosed herein may be conducted after producing or obtaining any aromatic hydrocarbon mixture containing xylenes. The xylenes present in the aromatic hydrocarbon mixture may represent an equilibrium mixture of xylenes or at least one xylene isomer may be produced in abundance compared to an equilibrium mixture. For instance, the aromatic hydrocarbon mixture may comprise p-xylene in a higher amount than an equilibrium mixture, preferably wherein p-xylene is a majority xylene isomer of the aromatic hydrocarbon mixture, and more preferably wherein p-xylene is a majority component of the aromatic hydrocarbon mixture. Illustrative aromatic hydrocarbon mixtures may comprise at least about 50 wt % xylenes, or at least about 60 wt % xylenes, or at least about 70 wt % xylenes, or at least about 80 wt % xylenes, based on total mass of the aromatic hydrocarbon mixture.

The aromatic hydrocarbon mixture may be produced or obtained from any suitable source of aromatic hydrocarbons. In non-limiting examples, the aromatic hydrocarbon mixture may be produced by performing catalytic alkylation on benzene and/or toluene using methanol and/or dimethyl ether as an alkylating agent. Such catalytic alkylation processes, described further below, may be advantageous by providing high selectivity for p-xylene. The benzene and/or toluene may, in turn, be obtained from a reforming process producing a reformate stream. As such, the separation processes disclosed herein may be coupled to a reforming process in at least this respect. Moreover, as discussed further hereinafter, a $C_{8+}$ aromatics stream obtained from reforming may be processed in parallel to the xylene separation processes disclosed herein to realize various advantages in the present disclosure.

Reforming processes may produce a reformate stream comprising $C_6$+ hydrocarbons, such as a mixture of non-aromatic hydrocarbons, lower aromatic hydrocarbons (i.e., benzene and/or toluene), ethylbenzene, an equilibrium mixture of xylenes ($C_8$ aromatic hydrocarbons), and $C_{9+}$ aromatic hydrocarbons. A reformate stream suitable for further processing according to the disclosure herein may be obtained by providing a feed stream comprising paraffins and/or naphthenes into a reformer under conditions suitable to convert at least a portion of the paraffins and/or naphthenes into one or more aromatic hydrocarbons (i.e., one or more of benzene, toluene, ethylbenzene, xylenes, and $C_{9+}$ aromatic hydrocarbons). Reforming may be conducted in the presence of a reforming catalyst under suitable reforming conditions. Illustrative reforming conditions may include, for example, a temperature ranging from about 427° C. to about 565° C. (about 800° F. to about 1050° F.), a pressure ranging from about 241 kilopascal (gauge) to about 3447 kilopascal (gauge) (from about 35 psig to about 500 psig), and a liquid hourly space velocity ("LHSV") ranging from about 0.3 $hr^{-1}$ to about 3.0 $hr^{-1}$, to produce a reformate stream comprising one or more of the foregoing aromatic hydrocarbons. Preferably, reforming is performed under high severity reforming conditions including a temperature of about 527° C. to about 543° C. (about 980° F. to about 1010° F.), which may result in a low concentration of linear paraffins and a high octane number of the reformate stream. Illustrative processes and catalysts useful for reforming linear/branched paraffins and naphthenes to produce aromatic hydrocarbons and high octane number liquid products can be found in, for example, Catalytic Reforming, by Donald M Little, Penn Well Publishing Company (1985), the relevant contents of which are incorporated herein by reference in its entirety. The feed stream provided for reforming may be derived from, for example, a crude distillation column, a crude cracker effluent, a stream cracker effluent, a fluid catalytic cracker ("FCC") effluent, the like, and any combination thereof.

A reformate stream may be separated, such as through distillation and/or extraction, into a $C_{8+}$ aromatics stream and a lower aromatic hydrocarbon stream, such as at least one of a benzene stream, a toluene stream, or a mixed benzene/toluene stream. The benzene and/or toluene in the lower aromatic hydrocarbon stream may be further reacted, as discussed further above, to produce the aromatic hydrocarbon mixture comprising xylenes, which may be further separated according to the disclosure herein. Non-aromatic compounds may be present in the lower aromatic hydrocarbon stream and may be separated therefrom prior to conversion of the benzene and/or toluene into xylenes, as discussed further herein. Preferably, the lower aromatic hydrocarbon stream is substantially free of non-aromatic compounds before being converted into xylenes. To ensure that the lower aromatic hydrocarbon stream is substantially free of non-aromatic compounds, solvent extraction may be performed after separating the lower aromatic hydrocarbon stream and the $C_{8+}$ aromatics stream from each other. As discussed further hereinbelow, xylenes in the $C_{8+}$ aromatics stream may be processed in parallel with xylenes being separated from the aromatic hydrocarbon mixture to achieve an overall high conversion of feed stream to xylene products.

The lower aromatic hydrocarbon stream obtained from a reformate stream may be further processed to benzene and/or toluene suitable for being converted into an aromatic hydrocarbon mixture comprising xylenes, which may be subsequently separated from one another in accordance with the disclosure herein. Further processing of the lower aromatic hydrocarbon stream is addressed hereinafter.

Prior to being converted into an aromatic hydrocarbon mixture comprising xylenes, the lower aromatic hydrocarbon stream may be processed to remove non-aromatic compounds therefrom. Removal of non-aromatic compounds from benzene and/or toluene may take place via liquid-liquid extraction, extractive distillation, or any combination thereof. Non-aromatic compounds removed from the lower aromatic hydrocarbon stream may be utilized in other hydrocarbon processing operations (e.g., olefin oligomerization, alkylation, cracking, or the like) or as fuel for these or other processes. Following extraction or extractive distillation, the remaining benzene and/or toluene feed may be subsequently converted into an aromatic hydrocarbon mixture comprising xylenes for further separation according to the disclosure herein.

Toluene and/or benzene in the lower aromatic hydrocarbon stream may be further reacted under alkylation conditions to form an aromatic hydrocarbon mixture comprising mixed xylenes, preferably a non-equilibrium xylenes mixture in which p-xylene is the predominant xylene isomer, which may be further separated according to the disclosure herein. More specifically, processes of the present disclosure may comprise contacting toluene and/or benzene with an alkylating agent comprising methanol and/or dimethyl ether in the presence of an alkylation catalyst in an alkylation reactor under alkylation conditions to produce an alkylation stream comprising o-xylene, m-xylene, p-xylene, styrene, $C_{9+}$ aromatic hydrocarbons, and toluene, and obtaining at least a portion of the aromatic hydrocarbon mixture from the alkylation stream.

Benzene, if present in the lower aromatic hydrocarbon stream, may be converted to toluene under the alkylation conditions and obtained in the alkylation stream. Toluene present in the alkylation stream may be separated and recycled to the alkylation reactor to convert the toluene into a further quantity of o-xylene, m-xylene, p-xylene, styrene, and $C_{9+}$ aromatic hydrocarbons. As such, obtaining at least a portion of the aromatic hydrocarbon mixture from the alkylation stream may further comprise separating the alkylation stream into a toluene-rich stream and a $C_{8+}$ aromatic hydrocarbon stream; recycling the toluene-rich stream to the alkylation reactor; and providing the $C_{8+}$ aromatic hydrocarbon stream as at least a portion of the aromatic hydrocarbon mixture from which xylenes are then separated according to the disclosure herein.

The alkylation reactor producing the $C_{8+}$ aromatic hydrocarbons from the lower aromatic hydrocarbon stream may be a fluidized bed reactor, which may produce styrene as a byproduct under the alkylation reaction conditions. In a fluidized bed reactor under suitable alkylation conditions, the $C_{8+}$ aromatic hydrocarbon stream may comprise styrene at a concentration up to about 5000 ppm by weight, based on total mass of the $C_{8+}$ aromatic hydrocarbon stream.

Lower aromatic hydrocarbons may be alkylated (e.g., methylated) by contacting a lower aromatic hydrocarbon with an alkylating agent comprising methanol and/or dimethyl ether in the presence of an alkylation catalyst in an alkylation reactor under alkylation conditions. Alkylation of benzene may produce toluene. Toluene may be alkylated to produce xylenes, which may over-alkylate to produce $C_{9+}$ aromatic hydrocarbons. The alkylation catalyst and alkylation conditions may be chosen such that the alkylation stream (aromatic hydrocarbon mixture) obtained from the alkylation reactor comprises a non-equilibrium mixture of xylenes. For example, the aromatic hydrocarbon mixture may comprise p-xylene at a high concentration, and o-xylene, m-xylene, and styrene at relatively low concentrations. Description of exemplary methylation catalysts, methylation agents, and methylation conditions can be found in, for example, U.S. Pat. Nos. 6,423,879; 6,504,072; 6,642,426, and 9,440,893, the relevant contents of which are incorporated herein by reference. Due to their high p-xylene concentration, aromatic hydrocarbon mixtures formed under reaction conditions producing a non-equilibrium xylenes mixture may be advantageous for further xylenes separation according to the disclosure herein. For example, such aromatic hydrocarbon mixtures may facilitate separation of p-xylene and m-xylene from one another in satisfactory purity levels and without requiring m-xylene recycling to increase overall p-xylene yields. At a minimum, the fourth stream comprising m-xylene may be a useful high-octane fuel blend component, such as for AvGas. By eliminating such recycling operations, byproducts such as styrene and phenol in the aromatic hydrocarbon mixture may be more readily tolerated, as discussed herein.

In non-limiting examples, an aromatic hydrocarbon mixture obtained from methylation of lower aromatic hydrocarbons with methanol and/or dimethyl ether may feature: an o-xylene concentration from c(oX)1 wt % to c(oX)2 wt %, based on the total mass of the aromatic hydrocarbon mixture, wherein c(oX)1 and c(oX)2 can be, independently, for example, 0, 0.02, 0.04, 0.01, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(oX)1<c(oX)2; an m-xylene concentration from c(mX)1 wt % to c(mX)2 wt %, based on the total mass of the aromatic hydrocarbon mixture, wherein c(mX)1 and c(mX)2 can be, independently, for example, 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(mX)1<c(mX)2; a p-xylene concentration from c(pX)1 wt % to c(pX)2 wt %, based on the total mass of the aromatic hydrocarbon mixture, wherein c(pX)1 and c(pX)2 can be, independently, for example, 25, 30, 35, 40, 45, 50, 55, 60, 65, 70, 75, 80, 85, 90, 91, 92, 93, 94, 95, as long as c(pX)1<c(pX)2; an m-xylene/o-xylene ratio from r(m/o)1 to r(m/o)2, where r(m/o)1 and r(m/o)2 can be, independently, for example, 2.1, 2.5, 3.0, 3.5, 4.0, 4.5, 5.0, 6.0, 7.0, 7.5, 8.0, 9.0, 10, 11, 12, 12.5, 13, 14, 15, 16, 17, 17.5, 18, 19, 20, as long as r(m/o) 1<r(m/o)2; and an ethylbenzene concentration from c(EB)1 wt % to c(EB)2 wt %, based on the total mass of the aromatic hydrocarbon mixture, wherein c(EB)1 and c(EB)2 can be, independently, for example, 0, 0.02, 0.04, 0.05, 0.06, 0.08, 0.1, 0.2, 0.4, 0.5, 0.6, 0.8, 1, 2, 3, 4, 5, as long as c(EB) 1<c(EB)2. The alkylation reaction can be advantageously conducted under alkylation conditions employing relatively low reactor temperatures, such as for example, less than or equal to about 500° C., less than or equal to about 475° C., less than or equal to about 450° C., less than or equal to about 425° C., or less than or equal to about 400° C. Alkylation may be conducted at temperatures of greater than or equal to about 200° C., greater than or equal to about 250° C., or greater than or equal to about 300° C. In illustrative embodiments, suitable temperature ranges may include temperatures ranging from about 200° C. to about 500° C., about 275° C. to about 475° C., about 300° C. to about 450° C., or about 250° C. to about 400° C. Such low-temperature reactions can be particularly utilized when a MWW framework type zeolite is present as the alkylation catalyst.

Operating pressures in the alkylation reactor can vary in a broad range, such as for example, from ≥100 kPa, ≥1000 kPa, ≥1500 kPa, ≥2000 kPa, ≥3000 kPa, or ≥3500 kPa, to ≤8500 kPa, such as ≤7000 kPa, or ≤6000 kPa. In some examples, operating pressures may range from 700 kPa to 7000 kPa, such as from 1000 kPa to 6000 kPa, or from 2000 kPa to 5000 kPa.

WHSV values based on total aromatic hydrocarbon feed and alkylation agent feed may be in a range from, for example, 0.5 $hr^{-1}$ to 50 $hr^{-1}$, such as from 5 $hr^{-1}$ to 15 $hr^{-1}$, from 1 $hr^{-1}$ to 10 $hr^{-1}$, or from 5 $hr^{-1}$ to 10 $hr^{-1}$, or from 6.7 $hr^{-1}$ to 10 $hr^{-1}$. In some embodiments, at least part of the lower aromatic hydrocarbons, the alkylating agent and/or the aromatic hydrocarbon mixture may be present in the alkylation reactor in a liquid phase.

The alkylation reactor may comprise any suitable reactor system comprising, but not limited to, a fixed bed reactor, a moving bed reactor, a fluidized bed reactor, and/or a reactive distillation unit. In addition, the reactor may include a single alkylation reaction zone or multiple alkylation reaction zones therein. Injection of the alkylating agent can be effected at a single point in the alkylation reactor or at multiple points spaced along the alkylation reactor. The lower aromatic hydrocarbons and the alkylating agent may be premixed before entering the alkylation reactor or be introduced separately.

Any suitable catalyst capable of converting toluene (or benzene) to xylenes with an alkylating agent can be used for alkylation in this disclosure. Examples of such catalysts are crystalline microporous materials including zeolite-based, as well as non-zeolite-based, molecular sieves and can be of the large, medium, or small pore type. Molecular sieves can have 3-dimensional, four-connected framework structure of corner-sharing [$TO_4$] tetrahedra, where T can be a tetrahedrally coordinated atom. These molecular sieves are often described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al, Introduction to Zeolite Science and Practice, Second Completely Revised and Expanded Edition, Volume 137, pages 1-67, Elsevier Science, B.V., Amsterdam, Netherlands (2001). Another convenient measure of the extent to which a molecular sieve provides control of molecules of varying sizes to its internal structure is the Constraint Index. The method by which Constraint Index is determined is described fully in U.S. Pat. No. 4,016,218, which is incorporated herein by reference for details of the method.

Non-limiting examples of molecular sieves include small pore molecular sieves (e.g., AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof), medium pore molecular sieves (e.g., AFO, AEL, EUO, HEU, FER, MEL, MFI, MTW, MTT, TON, and substituted forms thereof), large pore molecular sieves (e.g., EMT, FAU, and substituted forms thereof), intergrowths thereof, and combinations thereof. Other molecular sieves include, but are not limited to, ANA, BEA, CFI, CLO, DON, GIS, LTL, MER, MOR, MWW, SOD, intergrowths thereof, and combinations thereof. In some embodiments, the molecular sieve has an MWW framework type (morphology).

The small, medium, and large pore molecular sieves have from a 4-ring to a 12-ring or greater framework-type. In some embodiments, the zeolitic molecular sieves have 6-, 8-, 10-, or 12-ring structures and an average pore size in the range from about 3 Å to 15 Å. In other embodiments, the molecular sieves are aluminosilicate molecular sieves and have a 6-ring or an 8-ring structure and an average pore size of about 5 Å or less, such as in the range from 3 Å to about 5 Å, for example from 3 Å to about 4.5 Å or from 3.5 Å to about 4.2 Å.

Other non-limiting examples of zeolitic and non-zeolitic molecular sieves include one or a combination of the following: Beta (U.S. Pat. No. 3,308,069 and Reissue No. 28,341), ZSM-3 (U.S. Pat. No. 3,415,736), ZSM-4 (U.S. Pat. No. 4,021,947), ZSM-5 (U.S. Pat. Nos. 3,702,886, 4,797,267 and 5,783,321), ZSM-11 (U.S. Pat. No. 3,709, 979), ZSM-12 (U.S. Pat. No. 3,832,449), ZSM-12 and ZSM-38 (U.S. Pat. No. 3,948,758), ZSM-14 (U.S. Pat. No. 3,923,636), ZSM-18 (U.S. Pat. No. 3,950,496), ZSM-20 (U.S. Pat. No. 3,972,983), ZSM-22 (U.S. Pat. No. 5,336, 478), ZSM-23 (U.S. Pat. No. 4,076,842), ZSM-34 (U.S. Pat. No. 4,086,186), ZSM-35 (U.S. Pat. No. 4,016,245), ZSM-38, ZSM-48 (U.S. Pat. No. 4,397,827), ZSM-50, ZSM-58 (U.S. Pat. No. 4,698,217), MCM-1 (U.S. Pat. No. 4,639, 358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880, 611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362, 697), ALPO-11 (U.S. Pat. No. 4,310,440), ultrastable Y zeolite (USY) (U.S. Pat. Nos. 3,293,192 and 3,449,070), Dealuminized Y zeolite (Deal Y) (U.S. Pat. No. 3,442,795), mordenite (naturally occurring and synthetic) (for synthetic mordenite U.S. Pat. Nos. 3,766,093 and 3,894,104), SSZ-13, titanium aluminosilicates (TASOs) such as TASO-45 (European Patent No. EP-A-0 229 295), boron silicates (U.S. Pat. No. 4,254,297), titanium aluminophosphates (TAPOs) (U.S. Pat. No. 4,500,651), mixtures of ZSM-5 and ZSM-11 (U.S. Pat. No. 4,229,424), ECR-18 (U.S. U.S. Pat. No. 5,278,345), SAPO-34 bound ALPO-5 (U.S. Pat. No. 5,972,203), those disclosed in International Publication No. WO 98/57743 published Dec. 23, 1988 (molecular sieve and Fischer-Tropsch), those disclosed in U.S. Pat. No. 6,300,535 (MFI-bound zeolites), mesoporous molecular sieves (U.S. Pat. Nos. 6,284,696, 5,098,684, 5,102,643 and 5,108,725), and the like, and intergrowths and/or combinations thereof.

In an embodiment, the methylation catalyst comprises an aluminosilicate catalyst composition. Aluminosilicates, as used herein, can include those having a molar relationship of $X_2O_3$:(n)$YO_2$ (wherein X is a trivalent element, e.g., Al; and Y is a tetravalent element, e.g., Si), in which n≤500, such as ≤250, ≤100, such as from 30 to 100.

Non-limiting examples of trivalent X can include aluminum, boron, iron, indium, gallium, and combinations thereof, for example X can be aluminum. Non-limiting examples of tetravalent Y can include silicon, tin, titanium, germanium, and combinations thereof, for example Y can be silicon.

Other non-limiting examples of aluminosilicate catalysts and compositions can be found, for instance, in U.S. Patent Application Publication No. 2003/0176751 and U.S. patent application Ser. No. 11/017,286 (filed Dec. 20, 2004) and 60/731,846 (filed Oct. 31, 2005).

One class of molecular sieve suitable for use in a process of this disclosure has a Constraint Index≤5, and is crystalline microporous material of the MWW framework type. In at least one embodiment, the crystalline microporous material is a zeolite. As used herein, the term "crystalline microporous material of the MWW framework type" includes one or more of:

(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, incorporated herein by reference);

(b) molecular sieves made from a second degree building block, being a 2-dimensional tiling of such MWW framework topology unit cells, forming a monolayer of one unit cell thickness, in an embodiment, one c-unit cell thickness;

(c) molecular sieves made from common second degree building blocks, being layers of one or more than one unit cell thickness, where the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and (d) molecular sieves made by any regular or random 2-dimensional or 3-dimensional combination of unit cells having the MWW framework topology.

Crystalline microporous materials of the MWW framework type include those molecular sieves having an X-ray diffraction pattern comprising d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (U.S. Pat. No. 4,954,325), PSH-3 (U.S. Pat. No. 4,439,409), SSZ-25 (U.S. Pat. No. 4,826,667), ERB-1 (European Patent No. 0293032), ITQ-1 (U.S. Pat. No. 6,077,498), ITQ-2 (International Publication No. WO97/17290), MCM-36 (U.S. Pat. No. 5,250,277), MCM-49 (U.S. Pat. No. 5,236,575), MCM-56 (U.S. Pat. No. 5,362,697), UZM-8 (U.S. Pat. No. 6,756,030), UZM-8HS (U.S. Pat. No. 7,713,513), UZM-37 (U.S. Pat. No. 7,982,084), EMM-10 (U.S. Pat. No. 7,842,277), EMM-12 (U.S. Pat. No. 8,704,025), EMM-13 (U.S. Pat. No. 8,704,023), UCB-3 (U.S. Pat. No. 9,790,143B2) and mixtures thereof.

In some embodiments, the crystalline microporous material of the MWW framework type may be contaminated with other crystalline materials, such as ferrierite or quartz. These contaminants may be present in quantities of ≤10 wt %, such as ≤5 wt %.

In some embodiments, the molecular sieves are not subjected to pre-treatments, such as high temperature steaming, to modify their diffusion properties. In other embodiments, the molecular sieves may be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350° C. to 550° C. A suitable silica-selectivation procedure is described in U.S. Pat. No. 5,476,823. In another embodiment, the catalyst is selectivated by contacting the catalyst with steam. Steaming of the zeolite is effected at a temperature of ≥950° C., such as from 950° C. to 1075° C., or from 1000° C. to 1050° C., for 10 minutes to 10 hours, such as from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026. In some embodiments, a combination of silica selectivation and coke selectivation may be employed.

It may be desirable to combine the molecular sieve, prior to selectivating, with at least one oxide modifier, such as at least one oxide selected from elements of Groups 2 to 4 and 13 to 16 of the Periodic Table. In some embodiments, the oxide modifier is selected from oxides of boron, magnesium, calcium, lanthanum, and phosphorus. In some cases, the molecular sieve may be combined with more than one oxide modifier, for example a combination of oxides of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be from 0.05 wt % and 20 wt %, such as from 0.1 wt % to 10 wt %, based on the weight of the final catalyst. Where the modifier comprises phosphorus, incorporation of modifier into the catalyst is conveniently achieved by the methods described in U.S. Pat. Nos. 4,356,338; 5,110,776; 5,231,064; and 5,348,643.

The molecular sieves may be used as the methylation catalyst without any binder or matrix, in a self-bound form. Alternatively, the molecular sieves may be composited with another material which is resistant to the temperatures and other conditions employed in the methylation reaction. Such binder or matrix materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels comprising mixtures of silica and metal oxides. Clays may also be included with the oxide type binders to modify the mechanical properties of the catalyst or to assist in its manufacture. Use of a material in conjunction with the molecular sieve whether combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, for example, bentonite and kaolin, to improve the crush strength of the catalyst under commercial operating conditions and function as binders or matrices for the catalyst. The relative proportions of molecular sieve and inorganic oxide matrix vary widely, with the sieve content ranging from 1 wt % to 90 wt %, and in some embodiments the composite is prepared in the form of beads, in the range of 2 wt % to 80 wt % of the composite.

As indicated above, a $C_{8+}$ aromatics stream obtained from a reforming process may comprise xylene isomers and may be desirably processed in a xylenes loop (see FIG. 2 above) in parallel with the separation process for an aromatic hydrocarbon mixture described herein to increase the overall extent of xylene recovery. The xylenes loop may comprise a xylenes splitter producing a $C_8$ aromatics stream, a p-xylene separation unit producing a p-xylene stream and a raffinate stream depleted in p-xylene (a raffinate stream or a filtrate stream, depending on how the stream is produced), and a xylenes isomerization unit that may isomerize the raffinate stream depleted in p-xylene to produce an isomerized stream comprising an additional amount of p-xylene, namely p-xylene at a higher concentration than the raffinate stream. The isomerized stream may be at least partly recycled to the xylenes splitter and/or the p-xylene separation unit. The isomerization unit may comprise an isomerization reactor operated under vapor phase conditions and/or under liquid phase conditions.

In non-limiting examples, the $C_{8+}$ aromatics stream obtained from the reformate splitter may comprise ethylbenzene at a concentration of about c(EB)1 wt % to c(EB)2 wt %, based on the total mass of the raffinate stream, where c(EB)1 and c(EB)2 can be, independently, for example, 0, 0.02, 0.04, 0.05, 0.06, 0.08, 0.1, 0.2, 0.4, 0.5, 0.6, 0.8, 1, 2, 3, 4, 5, 6, 8, 10, 12, 14, 15, 16, 18, 20, 22, 24, 25, 26, 28, 30, as long as c(EB)1<c(EB)2. When the $C_{8+}$ aromatics stream also comprises ethylbenzene at a sufficiently high concentration, such as greater than or equal to about 5 wt %, or greater than or equal to about 8 wt %, or greater than or equal to about 10 wt %, it may be desirable to remove at least a portion of the ethylbenzene prior to processing in the p-xylene separation unit. Exemplary ethylbenzene conversion catalysts and processes therefor can be found, for example, in U.S. Pat. No. 5,977,420, the relevant contents of which are incorporated herein by reference. Optionally, operations for removing at least a portion of the ethylbenzene may comprise a solvent extraction step. The resulting processed $C_{8+}$ aromatics stream may have an ethylbenzene concentration that is suitably small for further processing to isolate xylenes therefrom according to the disclosure herein.

As indicated above, the $C_{8+}$ aromatics stream obtained from a reformate stream via a reformate splitter may be processed separately from the aromatic hydrocarbon mixture produced by alkylating lower aromatic hydrocarbons. Prior to separating the xylene isomers from each other, the $C_{8+}$ aromatics stream may be further separated, such as in a xylenes splitter, to obtain a $C_8$ aromatics stream comprising at least o-xylene, m-xylene and p-xylene. The $C_8$ aromatics stream obtained from the xylenes splitter may comprise an equilibrium xylenes mixture in particular examples. The $C_8$ aromatics stream can be then fed into the p-xylene separation unit comprising a simulated bed chromatography separation unit and/or a crystallization separation unit described above to produce a p-xylene stream and a stream depleted in p-xylene (either a raffinate or a filtrate stream, depending on how produced).

The stream depleted in p-xylene may be exposed to catalytic isomerization conditions in an isomerization unit to obtain a recycle stream comprising, for example, an equilibrium mixture of o-xylene, m-xylene, and p-xylene. The recycle stream may be at least partly returned to the xylenes splitter and/or to the p-xylene separation unit. The xylenes loop thus permits production of p-xylene from m-xylene and o-xylene that may be present in the $C_{8+}$ aromatics stream obtained from the reformate splitter.

The isomerization conditions used to convert the stream depleted in p-xylene into an equilibrium xylenes mixture may include a temperature and a pressure such that a majority of the xylenes are in a vapor phase ("vapor-phase isomerization" or "VPI"). Alternatively, the isomerization conditions may include a temperature and a pressure such that a majority of the xylenes are in liquid phase ("liquid-phase isomerization" or "LPI"). LPI requires a lower temperature than VPI, and can be carried out without co-feeding a molecular hydrogen stream. As such, LPI may be preferred over VPI, especially when ethylbenzene is present at a low concentration. VPI may be favored when ethylbenzene is present at a high concentration, for example, greater than or equal to about 10 wt %, based on the total mass, because VPI can be more effective than LPI in converting ethylbenzene. Description of exemplary VPI processes and catalysts can be found in, for example, U.S. Patent Application Publications 2011/03196881; 2012/0108867; 2012/0108868; 2014/0023563; 2015/0051430; and 2017/0081259, the relevant contents of which are incorporated herein by reference. Description of exemplary LPI processes and catalysts can be found in, for example, U.S. Patent Application Publications 2011/0319688; 2012/0108867; 2013/0274532; 2014/0023563; and 2015/0051430, the relevant contents of which are incorporated herein by reference.

Optionally, o-xylene and/or m-xylene produced from alkylation of lower aromatic hydrocarbons and separated according to the disclosure herein may be further exposed to the isomerization conditions in order to at least partially convert these components to p-xylene as well. That is, processes of the present disclosure may further comprise exposing at least a portion of the first stream and/or at least a portion of the fourth stream to the catalytic isomerization conditions suitable for converting o-xylene and m-xylene into a mixture of xylene isomers. If so performed, phenol and/or styrene may be removed from the first stream and/or the fourth stream to protect the isomerization catalyst. Suitable techniques for mitigating phenol and/or styrene include those mentioned above.

In view of the foregoing, one or more embodiments of the processes disclosed herein may comprise: providing a $C_{8+}$ aromatic hydrocarbon mixture comprising at least o-xylene, m-xylene, p-xylene, styrene, optionally phenol, and $C_{9+}$ aromatic hydrocarbons; wherein the $C_{8+}$ aromatic hydrocarbon mixture comprises at least about 50 wt % p-xylene, based on total mass of the $C_{8+}$ aromatic hydrocarbon mixture; distilling the $C_{8+}$ aromatic hydrocarbon mixture to form a first stream enriched in o-xylene, styrene and $C_{9+}$ aromatic hydrocarbons and lean in m-xylene and p-xylene relative to the $C_{8+}$ aromatic hydrocarbon mixture, and a second stream enriched in m-xylene and p-xylene and lean in o-xylene relative to the $C_{8+}$ aromatic hydrocarbon mixture; and separating the second stream into a third stream enriched in p-xylene and lean in m-xylene relative to the second stream and a fourth stream comprising m-xylene.

Embodiments disclosed herein include:

A. Xylene separation processes. The processes comprise: providing an aromatic hydrocarbon mixture comprising at least o-xylene, m-xylene, and p-xylene; separating the aromatic hydrocarbon mixture into a first stream enriched in o-xylene and lean in m-xylene and p-xylene relative to the aromatic hydrocarbon mixture, and a second stream enriched in m-xylene and p-xylene and lean in o-xylene relative to the aromatic hydrocarbon mixture; and separating the second stream into a third stream enriched in p-xylene and lean in m-xylene relative to the second stream and a fourth stream comprising m-xylene.

B. Aromatic hydrocarbon separation processes. The processes comprise: providing a $C_{8+}$ aromatic hydrocarbon mixture comprising at least o-xylene, m-xylene, p-xylene, styrene, optionally phenol, and $C_{9+}$ aromatic hydrocarbons; wherein the $C_{8+}$ aromatic hydrocarbon mixture comprises at least about 50 wt % p-xylene, based on total mass of the $C_{8+}$ aromatic hydrocarbon mixture; distilling the $C_{8+}$ aromatic hydrocarbon mixture to form a first stream enriched in o-xylene, styrene and $C_{9+}$ aromatic hydrocarbons and lean in m-xylene and p-xylene relative to the $C_{8+}$ aromatic hydrocarbon mixture, and a second stream enriched in m-xylene and p-xylene and lean in o-xylene relative to the $C_{8+}$ aromatic hydrocarbon mixture; and separating the second stream into a third stream enriched in p-xylene and lean in m-xylene relative to the second stream and a fourth stream comprising m-xylene.

Embodiments A and B may have one or more of the following additional elements in any combination:

Element 1: wherein separating the aromatic hydrocarbon mixture into the first stream and the second stream takes place in a distillation column, the first stream being obtained as a bottoms fraction and the second stream being obtained as an overhead fraction.

Element 2: wherein the distillation column is a tray-based distillation column comprising at least about 140 separation trays.

Element 3: wherein the aromatic hydrocarbon mixture further comprises styrene, and at least a majority of the styrene present in the aromatic hydrocarbon mixture enters the bottoms fraction.

Element 4: wherein the aromatic hydrocarbon mixture comprises up to about 5000 ppm styrene by weight, based on total mass of the aromatic hydrocarbon mixture, and at least about 90% of the styrene present in the aromatic hydrocarbon mixture enters the bottoms fraction.

Element 5: wherein the aromatic hydrocarbon mixture further comprises $C_{9+}$ aromatic hydrocarbons, and at least a majority of the $C_{9+}$ aromatic hydrocarbons present in the aromatic hydrocarbon mixture enters the bottoms fraction.

Element 6: wherein the process further comprises separating the bottoms fraction into a fifth stream enriched in o-xylene relative to the first stream and a sixth stream enriched in $C_{9+}$ aromatic hydrocarbons relative to the first stream.

Element 7: wherein at least about 90% of the o-xylene present in the aromatic hydrocarbon mixture enters the first stream.

Element 7A: wherein at least about 95%, or at least about 98%, or at least about 99% of the o-xylene present in the aromatic hydrocarbon mixture enters the first stream.

Element 8: wherein the second stream comprises o-xylene at a concentration of about 3.5 wt % or less, based on total mass of the second stream.

Element 8A: wherein the second stream comprises o-xylene at a concentration of about 1 wt % or less, based on total mass of the second stream.

Element 9: wherein the second stream is separated into the third stream and the fourth stream using simulated moving bed chromatography.

Element 10: wherein the second stream is separated into the third stream and the fourth stream using crystallization.

Element 10A: wherein the second stream is separated into the third stream and the fourth stream using crystallization, the fourth stream comprising a mixture of m-xylene and p-xylene.

Element 11: wherein the fourth stream comprises a mixture of m-xylene and p-xylene.

Element 12: wherein the aromatic hydrocarbon mixture comprises p-xylene at a concentration of at least about 50 wt %, based on total mass of the aromatic hydrocarbon mixture.

Element 13: wherein the process further comprises contacting toluene and/or benzene with an alkylating agent comprising methanol and/or dimethyl ether in the presence of an alkylation catalyst in an alkylation reactor under alkylation conditions to produce an alkylation stream comprising o-xylene, m-xylene, p-xylene, styrene, $C_{9+}$ aromatic hydrocarbons, and toluene; and obtaining at least a portion of the aromatic hydrocarbon mixture from the alkylation stream.

Element 14: wherein the alkylation stream comprises toluene, and obtaining at least a portion of the aromatic hydrocarbon mixture from the alkylation stream comprises: separating the alkylation stream to obtain a toluene-rich stream and a $C_{8+}$ aromatic hydrocarbon stream; recycling the toluene-rich stream to the alkylation reactor; and providing the $C_{8+}$ aromatic hydrocarbon stream as at least a portion of the aromatic hydrocarbon mixture.

Element 15: wherein the alkylation reactor is a fluidized bed reactor, and the $C_{8+}$ aromatic hydrocarbon stream comprises styrene at a concentration up to about 5000 ppm by weight, based on total mass of the $C_{8+}$ aromatic hydrocarbon stream.

Element 16: wherein the toluene and/or benzene is obtained by: providing a reformate stream comprising $C_{6+}$ hydrocarbons; and separating the reformate stream into a $C_{8+}$ aromatics stream and a lower aromatic hydrocarbon stream comprising at least one of a benzene stream, a toluene stream, or a mixed benzene/toluene stream.

Element 17: wherein the process further comprises: separating the $C_{8+}$ aromatics stream in a xylenes splitter to obtain a $C_8$ aromatics stream comprising o-xylene, m-xylene, and p-xylene; separating the $C_8$ aromatics stream in a p-xylene separation unit to obtain a p-xylene stream and a raffinate stream depleted in p-xylene, and then exposing the raffinate stream to catalytic isomerization conditions in an isomerization unit to obtain an isomerized stream comprising p-xylene at a higher concentration than the raffinate stream; and recycling at least a portion of the isomerized stream to the xylenes splitter and/or at least a portion of the isomerized stream to the p-xylene separation unit.

Element 18: wherein the process further comprises exposing at least a portion of the first stream and/or at least a portion of the fourth stream to the catalytic isomerization conditions.

Element 19: wherein providing the $C_{8+}$ aromatic hydrocarbon mixture comprises: contacting toluene and/or benzene with an alkylating agent comprising methanol and/or dimethyl ether in the presence of an alkylation catalyst in an alkylation reactor under alkylation conditions to produce an alkylation stream comprising o-xylene, m-xylene, p-xylene, styrene, $C_{9+}$ aromatic hydrocarbons, and optionally toluene; and obtaining at least a portion of the $C_{8+}$ aromatic hydrocarbon mixture from the alkylation stream.

By way of non-limiting example, exemplary combinations applicable to A and B include, but are not limited to: 1 and 2; 1, and 3 or 4; 1 and 5; 1 and 6; 1, and 7 or 7A; 1, 7 or 7A, and 8 or 8A; 1, 8 or 8A, and 9; 1, 8 or 8A, and 10; 1 and 9; 1, and 10 or 10A; 1, 10, and 11; 1 and 12; 1 and 13; 1, 13, and 14; 1, 13 and 15; 1, 13, and 16; 1, 13, 14, and 17; 1, 13, 16, and 17; 1 and 18; 7 or 7A, and 8 or 8A; 7 or 7A, and 9; 7 or 7A, and 10 or 10A; 7 or 7A, and 12; 7 or 7A, and 13; 7 or 7A, 13, and 14; 7 or 7A, 13, and 15; 7 or 7A, 13, and 16; 7 or 7A, 13, 14, and 17; 7 or 7A, 13, 16, and 17; 7 or 7A, and 18; 8 or 8A, and 9; 8 or 8A, and 10 or 10A; 8 or 8A, and 12; 8 or 8A, and 13; 8 or 8A, 13, and 14; 8 or 8A, 13, and 15; 8 or 8A, 13, and 16; 8 or 8A, 13, 14, and 17; 8 or 8A, 13, 16, and 17; 8 or 8A, and 18; 9 and 12; 9 and 13; 9, 13, and 14; 9, 13, and 15; 9, 13, and 16; 9, 13, 14, and 17; 9, 13, 16, and 17; 9 and 18; 10 or 10A, and 12; 10 or 10A, and 13; 10 or 10A, 13, and 14; 10 or 10A, 13, and 15; 10 or 10A, 13, and 16; 10 or 10A, 13, 14, and 17; 10 or 10A, 13, 16, and 17; 10 or 10A, and 18; 12 and 13; 12, 13, and 14; 12, 13, and 15; 12, 13, and 16; 12, 13, 14, and 17; 12, 13, 16, and 17; and 12 and 18.

The present disclosure further relates to the following non-limiting embodiments:

A1: A process comprising:

providing an aromatic hydrocarbon mixture comprising at least o-xylene, m-xylene, and p-xylene;

separating the aromatic hydrocarbon mixture into a first stream enriched in o-xylene and lean in m-xylene and p-xylene relative to the aromatic hydrocarbon mixture, and a second stream enriched in m-xylene and p-xylene and lean in o-xylene relative to the aromatic hydrocarbon mixture; and separating the second stream into a third stream enriched in p-xylene and lean in m-xylene relative to the second stream and a fourth stream comprising m-xylene.

A2: The process of A1, wherein separating the aromatic hydrocarbon mixture into the first stream and the second stream takes place in a distillation column, the first stream being obtained as a bottoms fraction and the second stream being obtained as an overhead fraction.

A3: The process of A2, wherein the distillation column is a tray-based distillation column comprising at least about 140 separation trays.

A4: The process of A2 or A3, wherein the aromatic hydrocarbon mixture further comprises styrene, and at least a majority of the styrene present in the aromatic hydrocarbon mixture enters the bottoms fraction.

A5: The process of A4, wherein the aromatic hydrocarbon mixture comprises up to about 5000 ppm styrene by weight, based on total mass of the aromatic hydrocarbon mixture, and at least about 90% of the styrene present in the aromatic hydrocarbon mixture enters the bottoms fraction.

A6: The process of any of A2 to A5, wherein the aromatic hydrocarbon mixture further comprises $C_{9+}$ aromatic hydrocarbons, and at least a majority of the $C_{9+}$ aromatic hydrocarbons present in the aromatic hydrocarbon mixture enters the bottoms fraction.

A7: The process of A6, further comprising:

separating the bottoms fraction into a fifth stream enriched in o-xylene relative to the first stream and a sixth stream enriched in $C_{9+}$ aromatic hydrocarbons relative to the first stream.

A8: The process of any of A1 to A7, wherein at least about 90% of the o-xylene present in the aromatic hydrocarbon mixture enters the first stream.

A9: The process of any of A1 to A8, wherein the second stream comprises o-xylene at a concentration of about 3.5 wt % or less, based on total mass of the second stream.

A10: The process of any of A1 to A9, wherein the second stream comprises o-xylene at a concentration of about 1 wt % or less, based on total mass of the second stream.

A11: The process of any of A1 to A10, wherein the second stream is separated into the third stream and the fourth stream using simulated moving bed chromatography.

A12: The process of any of A1 to A10, wherein the second stream is separated into the third stream and the fourth stream using crystallization.

A13: The process of A12, wherein the fourth stream comprises a mixture of m-xylene and p-xylene.

A14: The process of any of A1 to A13, wherein the aromatic hydrocarbon mixture comprises p-xylene at a concentration of at least about 50 wt %, based on total mass of the aromatic hydrocarbon mixture.

A15: The process of any of A1 to A14, further comprising:

contacting toluene and/or benzene with an alkylating agent comprising methanol and/or dimethyl ether in the presence of an alkylation catalyst in an alkylation reactor under alkylation conditions to produce an alkylation stream comprising o-xylene, m-xylene, p-xylene, styrene, $C_{9+}$ aromatic hydrocarbons, and toluene; and obtaining at least a portion of the aromatic hydrocarbon mixture from the alkylation stream.

A16: The process of A15, wherein the alkylation stream comprises toluene, and obtaining at least a portion of the aromatic hydrocarbon mixture from the alkylation stream comprises:

separating the alkylation stream to obtain a toluene-rich stream and a $C_{8+}$ aromatic hydrocarbon stream;

recycling the toluene-rich stream to the alkylation reactor; and providing the $C_{8+}$ aromatic hydrocarbon stream as at least a portion of the aromatic hydrocarbon mixture A17: The process of A16, wherein the alkylation reactor is a fluidized bed reactor, and the $C_{8+}$ aromatic hydrocarbon stream comprises styrene at a concentration up to about 5000 ppm by weight, based on total mass of the $C_{8+}$ aromatic hydrocarbon stream.

A18: The process of any of A15 to A17, wherein the toluene and/or benzene is obtained by:

providing a reformate stream comprising $C_{6+}$ hydrocarbons; and separating the reformate stream into a $C_{8+}$ aromatics stream and a lower aromatic hydrocarbon stream comprising at least one of a benzene stream, a toluene stream, or a mixed benzene/toluene stream.

A19: The process of A18, further comprising:

separating the $C_{8+}$ aromatics stream in a xylenes splitter to obtain a $C_8$ aromatics comprising o-xylene, m-xylene, and p-xylene; stream separating the $C_8$ aromatics stream in a p-xylene separation unit to obtain a p-xylene stream and a raffinate stream depleted in p-xylene, and then exposing the raffinate stream to catalytic isomerization conditions in an isomerization unit to obtain an isomerized stream comprising p-xylene at a higher concentration than the raffinate stream; and recycling at least a portion of the isomerized stream to the xylenes splitter and/or at least a portion of the isomerized stream to the p-xylene separation unit.

A20: The process of A19, further comprising:

exposing at least a portion of the first stream and/or at least a portion of the fourth stream to the catalytic isomerization conditions.

B1: A process comprising:

providing a $C_{8+}$ aromatic hydrocarbon mixture comprising at least o-xylene, m-xylene, p-xylene, styrene, optionally phenol, and $C_{9+}$ aromatic hydrocarbons;

wherein the $C_{8+}$ aromatic hydrocarbon mixture comprises at least about 50 wt % p-xylene, based on total mass of the $C_{8+}$ aromatic hydrocarbon mixture;

distilling the $C_{8+}$ aromatic hydrocarbon mixture to form a first stream enriched in o-xylene, styrene and $C_{9+}$ aromatic hydrocarbons and lean in m-xylene and p-xylene relative to the $C_{8+}$ aromatic hydrocarbon mixture, and a second stream enriched in m-xylene and p-xylene and lean in o-xylene relative to the $C_{8+}$ aromatic hydrocarbon mixture; and separating the second stream into a third stream enriched in p-xylene and lean in m-xylene relative to the second stream and a fourth stream comprising m-xylene.

B2: The process of B1, wherein the second stream is separated into the third stream and the fourth stream using simulated moving bed chromatography.

B3: The process of B1, wherein the second stream is separated into the third stream and the fourth stream using crystallization, the fourth stream comprising a mixture of m-xylene and p-xylene.

B4: The process of any of B1 to B3, wherein providing the $C_{8+}$ aromatic hydrocarbon mixture comprises:

contacting toluene and/or benzene with an alkylating agent comprising methanol and/or dimethyl ether in the presence of an alkylation catalyst in an alkylation reactor under alkylation conditions to produce an alkylation stream comprising o-xylene, m-xylene, p-xylene, styrene, $C_{9+}$ aromatic hydrocarbons, and optionally toluene; and obtaining at least a portion of the $C_{8+}$ aromatic hydrocarbon mixture from the alkylation stream.

Many alterations, modifications, and variations will be apparent to one having ordinary skill in the art in light of the foregoing description without departing from the spirit or scope of the present disclosure and that when numerical limits and numerical upper limits are listed herein, ranges from any lower limit to any upper limit are contemplated.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A process comprising:

providing an aromatic hydrocarbon mixture comprising at least o-xylene, m-xylene, and p-xylene, and wherein the hydrocarbon mixture further comprises styrene, phenol, or both;

separating the aromatic hydrocarbon mixture into a first stream enriched in o-xylene and lean in m-xylene and p-xylene relative to the aromatic hydrocarbon mixture, wherein the first stream comprises at least a majority of the styrene, the phenol, or both, of the aromatic hydrocarbon mixture, and a second stream enriched in m-xylene and p-xylene and lean in o-xylene relative to the aromatic hydrocarbon mixture; and separating the second stream into a third stream enriched in p-xylene and lean in m-xylene relative to the second stream and a fourth stream comprising m-xylene.

2. The process of claim 1, wherein separating the aromatic hydrocarbon mixture into the first stream and the second stream takes place in a distillation column, the first stream being obtained as a bottoms fraction and the second stream being obtained as an overhead fraction.

3. The process of claim 2, wherein the distillation column is a tray-based distillation column comprising at least about 140 separation trays.

4. The process of claim 2, wherein the aromatic hydrocarbon mixture comprises up to about 5000 ppm styrene by weight, based on total mass of the aromatic hydrocarbon mixture, and at least about 90% of the styrene present in the aromatic hydrocarbon mixture enters the bottoms fraction.

5. The process of claim 2, wherein the aromatic hydrocarbon mixture further comprises C9+ aromatic hydrocarbons, and at least a majority of the C9+ aromatic hydrocarbons present in the aromatic hydrocarbon mixture enters the bottoms fraction.

6. The process of claim 5, further comprising:

separating the bottoms fraction into a fifth stream enriched in o-xylene relative to the first stream and a sixth stream enriched in C9+ aromatic hydrocarbons relative to the first stream.

7. The process of claim 1, wherein at least about 90% of the o-xylene present in the aromatic hydrocarbon mixture enters the first stream.

8. The process of claim 1, wherein the second stream comprises o-xylene at a concentration of about 3.5 wt % or less, based on total mass of the second stream.

9. The process of claim 1, wherein the second stream comprises o-xylene at a concentration of about 1 wt % or less, based on total mass of the second stream.

10. The process of claim 1, wherein the second stream is separated into the third stream and the fourth stream using simulated moving bed chromatography.

11. The process of claim 1, wherein the second stream is separated into the third stream and the fourth stream using crystallization.

12. The process of claim 11, wherein the fourth stream comprises a mixture of m-xylene and p-xylene.

13. The process of claim 1, wherein the aromatic hydrocarbon mixture comprises p-xylene at a concentration of at least about 50 wt %, based on total mass of the aromatic hydrocarbon mixture.

14. The process of claim 1, further comprising:

contacting toluene and/or benzene with an alkylating agent comprising methanol and/or dimethyl ether in a presence of an alkylation catalyst in an alkylation reactor under alkylation conditions to produce an alkylation stream comprising o-xylene, m-xylene, p-xylene, styrene, C9+ aromatic hydrocarbons, and toluene; and obtaining at least a portion of the aromatic hydrocarbon mixture from the alkylation stream.

15. The process of claim 14, wherein the alkylation stream comprises toluene, and obtaining at least a portion of the aromatic hydrocarbon mixture from the alkylation stream comprises:

separating the alkylation stream to obtain a toluene-rich stream and a C8+ aromatic hydrocarbon stream;

recycling the toluene-rich stream to the alkylation reactor; and providing the C8+ aromatic hydrocarbon stream as at least a portion of the aromatic hydrocarbon mixture.

16. The process of claim 15, wherein the alkylation reactor is a fluidized bed reactor, and the C8+ aromatic hydrocarbon stream comprises styrene at a concentration up to about 5000 ppm by weight, based on total mass of the C8+ aromatic hydrocarbon stream.

17. The process of claim 14, wherein the toluene and/or benzene is obtained by:

providing a reformate stream comprising C6+ hydrocarbons; and separating the reformate stream into a C8+ aromatics stream and a lower aromatic hydrocarbon stream comprising at least one of a benzene stream, a toluene stream, or a mixed benzene/toluene stream.

18. The process of claim 17, further comprising:

separating the C8+ aromatics stream in a xylenes splitter to obtain a C8 aromatics stream comprising o-xylene, m-xylene, and p-xylene;

separating the C8 aromatics stream in a p-xylene separation unit to obtain a p-xylene stream and a raffinate stream depleted in p-xylene, and then exposing the raffinate stream to catalytic isomerization conditions in an isomerization unit to obtain an isomerized stream comprising p-xylene at a higher concentration than the raffinate stream; and recycling at least a portion of the isomerized stream to the xylenes splitter and/or at least a portion of the isomerized stream to the p-xylene separation unit.

19. The process of claim 18, further comprising:

exposing at least a portion of the first stream and/or at least a portion of the fourth stream to the catalytic isomerization conditions.

20. A process comprising:

providing a C8+ aromatic hydrocarbon mixture comprising at least o-xylene, m-xylene, p-xylene, styrene, optionally phenol, and C9+ aromatic hydrocarbons; wherein:

the C8+ aromatic hydrocarbon mixture further comprises styrene, phenol, or both; and the C8+ aromatic hydrocarbon mixture comprises at least about 50 wt % p-xylene, based on total mass of the C8+ aromatic hydrocarbon mixture;

distilling the C8+ aromatic hydrocarbon mixture to form a first stream enriched in o-xylene, and C9+ aromatic hydrocarbons and lean in m-xylene and p-xylene relative to the C8+ aromatic hydrocarbon mixture, wherein the first stream comprises at least a majority of the styrene, the phenol, or both, of the C8+ aromatic hydrocarbon mixture;

distilling the C8+ aromatic hydrocarbon mixture to form a second stream enriched in m-xylene and p-xylene and lean in o-xylene relative to the C8+ aromatic hydrocarbon mixture; and separating the second stream into a third stream enriched in p-xylene and lean in m-xylene relative to the second stream and a fourth stream comprising m-xylene.

21. The process of claim 20, wherein the second stream is separated into the third stream and the fourth stream using simulated moving bed chromatography.

22. The process of claim 20, wherein the second stream is separated into the third stream and the fourth stream using crystallization, the fourth stream comprising a mixture of m-xylene and p-xylene.

23. The process of claim 20, wherein providing the C8+ aromatic hydrocarbon mixture comprises:

contacting toluene and/or benzene with an alkylating agent comprising methanol and/or dimethyl ether in a presence of an alkylation catalyst in an alkylation reactor under alkylation conditions to produce an alkylation stream comprising o-xylene, m-xylene, p-xylene, styrene, C9+ aromatic hydrocarbons, and optionally toluene; and obtaining at least a portion of the C8+ aromatic hydrocarbon mixture from the alkylation stream.

24. The process of claim 1, further comprising separating the o-xylene from the styrene, the phenol, or both, of the first stream.

* * * * *